United States Patent
Ihara et al.

(10) Patent No.: US 8,652,682 B2
(45) Date of Patent: Feb. 18, 2014

(54) IONIC COMPOUND, ELECTROLYTIC SOLUTION, ELECTROCHEMICAL DEVICE, AND BATTERY

(75) Inventors: Masayuki Ihara, Fukushima (JP); Hiroyuki Yamaguchi, Fukushima (JP); Tadahiko Kubota, Kanagawa (JP)

(73) Assignee: Sony Corporation, Tokyo (JP)

( * ) Notice: Subject to any disclaimer, the term of this patent is extended or adjusted under 35 U.S.C. 154(b) by 1167 days.

(21) Appl. No.: 11/872,389

(22) Filed: Oct. 15, 2007

(65) Prior Publication Data

US 2008/0118845 A1    May 22, 2008

(30) Foreign Application Priority Data

Nov. 22, 2006  (JP) ................. P2006-316153

(51) Int. Cl.
*H01M 10/056*   (2010.01)

(52) U.S. Cl.
USPC ........... 429/199; 429/188; 429/200; 429/338; 252/62.2

(58) Field of Classification Search
USPC ................. 429/121–347; 252/62.2
See application file for complete search history.

(56) References Cited

U.S. PATENT DOCUMENTS

| | | | |
|---|---|---|---|
| 5,534,370 A | 7/1996 | Kita et al. | |
| 7,012,124 B2 | 3/2006 | Angell et al. | |
| 2001/0033964 A1* | 10/2001 | Heider et al. | 429/188 |
| 2004/0034253 A1* | 2/2004 | Angell et al. | 568/6 |
| 2004/0063986 A1 | 4/2004 | Wietelmann et al. | |
| 2006/0127777 A1* | 6/2006 | Ihara et al. | 429/326 |
| 2006/0240327 A1 | 10/2006 | Xu et al. | |
| 2006/0269845 A1* | 11/2006 | Xu et al. | 429/326 |

FOREIGN PATENT DOCUMENTS

| | | |
|---|---|---|
| JP | 2007-127005 | 10/1980 |
| JP | 7-65843 | 3/1995 |
| JP | 2003-536229 | 12/2003 |
| JP | 2004-534735 | 11/2004 |
| JP | 2005-5114 | 1/2005 |
| JP | 2005-79057 | 3/2005 |
| JP | 2005-228565 | 8/2005 |
| JP | 2008-004534 | 1/2008 |
| WO | WO 2006/115681 | 11/2006 |

OTHER PUBLICATIONS

Japanese Office Action issued Aug. 7, 2012 for corresponding Japanese Appln. No. 2006-316153.
Japanese Office Action issued May 23, 2012, for corresponding Japanese Appln. No. 2006-316153.

* cited by examiner

*Primary Examiner* — Basia Ridley
*Assistant Examiner* — James Lee
(74) *Attorney, Agent, or Firm* — K&L Gates LLP

(57) ABSTRACT

A battery capable of improving the cycle characteristics is provided. The battery includes a cathode, an anode, and an electrolytic solution. The electrolytic solution is impregnated in a separator provided between the cathode and the anode. The electrolytic solution contains an ionic compound such as (2,2-difluoromalonate oxalate)lithium borate and [bis(3,3,3-trifluoromethyl)glycolate oxalate]lithium borate as an electrolyte salt. In the ionic compound, an anion has an asymmetric structure, and a ligand having an oxygen chelate structure in the anion has a halogen as an element. In the battery, the chemical stability of the electrolytic solution is improved, compared to a battery in which the electrolytic solution contains bis(oxalate)lithium borate or the like as an electrolyte salt.

12 Claims, 4 Drawing Sheets

IONIC COMPOUND, ELECTROLYTIC SOLUTION, ELECTROCHEMICAL DEVICE, AND BATTERY

CROSS REFERENCES TO RELATED APPLICATIONS

The present application claims priority to Japanese Patent Application JP 2006-316153 filed in the Japanese Patent Office on Nov. 22, 2006, the entire contents of which being incorporated herein by reference.

BACKGROUND

The present application relates to an ionic compound, an electrolytic solution using it, an electrochemical device using it, and a battery using it.

An ionic compound has been widely used in various fields. As an example, in the electrochemical device field, an ionic compound containing an anion such as $PF_6^-$ and $BF_4^-$ has been used as an electrolyte salt making much account of the solubility, the ion dissociation property and the like.

Of the electrochemical devices, in the field of the battery mainly used as a power source of electronic devices, particularly in the field of the secondary battery capable of being charged and discharged, research and development to improve the battery characteristics such as the capacity characteristics and the cycle characteristics are actively made. Specially, a secondary battery using insertion and extraction of lithium ions for charge and discharge reaction (so-called lithium ion secondary battery) or a secondary battery using precipitation and dissolution of lithium ions (so-called lithium metal secondary battery) is extremely prospective, since such a lithium ion secondary battery or such a lithium metal secondary battery can provide a higher energy density compared to the existing lead battery and the existing nickel cadmium battery.

In such a secondary battery, an electrolytic solution in which an electrolyte salt such as $LiPF_6$ is dissolved in an ester carbonate-based nonaqueous solvent such as propylene carbonate and a diethyl carbonate is widely used making much account of the electric conductivity, the electric potential stability and the like. As the electrolyte salt, $LiBF_4$, $LiCF_3SO_3$, $LiClO_4$, $LiAsF_6$, $LiN(CF_3SO_2)_2$, $LiN(C_2F_5SO_2)_2$, $LiN(C_4F_9SO_2)(CF_3SO_2)$ or the like is used in addition to $LiPF_6$. Further, in recent years, bis(oxalate)lithium borate, bis(salicylate)lithium borate, bis(malonate)lithium borate, (malonate oxalate)lithium borate, bis(succinate)lithium borate, (difluoro oxalate)lithium borate, (tetrafluoro oxalate) lithium borate or the like is used (for example, refer to Japanese Unexamined Patent Application Publication Nos. 07-065843, 2003-536229, 2004-534735, 2005-079057, and 2005-005114). It is proposed that bis(malonate)lithium borate, (malonate oxalate)lithium borate, or bis(succinate) lithium borate is used to improve the heat resistance and the like in the electrochemical device field.

However, the existing ionic compound is not sufficient yet in terms of the solubility and the chemical stability. Therefore, in the electrolytic solution and the electrochemical device using the existing ionic compound, the performances are limited accordingly. More specifically, sufficient chemical stability is not able to be obtained in the electrolytic solution, and sufficient cycle characteristics are not able to be obtained in the secondary battery.

SUMMARY

In view of the foregoing, it is desirable to provide an ionic compound capable of improving the solubility and the chemical stability pursuant to an embodiment.

Further, it is desirable to provide an electrolytic solution capable of improving the chemical stability pursuant to an embodiment.

Furthermore, it is desirable to provide an electrochemical device and a battery capable of improving the cycle characteristics pursuant to an embodiment.

According to an embodiment, there is provided an ionic compound having a structure shown in Chemical formula 1.

Chemical formula 1

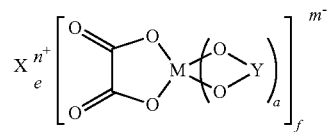

where $X^{n+}$ represents an ion of a Group 1A element or a Group 2A element in the short period periodic table, or an onium ion; M represents a transition metal, or a Group 3B element, a Group 4B element or a Group 5B element in the short period periodic table; Y represents —OC—$(CR1_2)_b$—CO—, —$R3_2$C—$(CR2_2)_c$—CO—, —$R3_2$C—$(CR2_2)_c$—$CR3_2$—, —$R3_2$C—$(CR2_2)_c$—$SO_2$—, —$O_2$S—$(CR2_2)_d$—$SO_2$— or —OC—$(CR2_2)_d$—$SO_2$—; R1 and R3 represent a hydrogen group, an alkyl group, a halogen group, or a halogenated alkyl group and are respectively identical or different, but at least one of R1 and R3 is respectively a halogen group or a halogenated alkyl group; R2 represents a hydrogen group, an alkyl group, a halogen group, or a halogenated alkyl group, and are identical or different; a, f, and n represent an integer number of 1 or 2; b and d represent one of integer numbers 1 to 4; c represents 0 or one of integer numbers 1 to 4; and e and m represent one of integer numbers 1 to 3.

According to an embodiment, there is provided an electrolytic solution containing a solvent and an electrolyte salt, wherein the electrolyte salt contains an ionic compound having a structure shown in Chemical formula 1.

Chemical formula 1

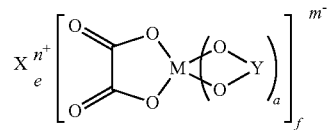

where $X^{n+}$ represents an ion of a Group 1A element or a Group 2A element in the short period periodic table, or an onium ion; M represents a transition metal, or a Group 3B element, a Group 4B element or a Group 5B element in the short period periodic table; Y represents —OC—$(CR1_2)_b$—CO—, —$R3_2$C—$(CR2_2)_c$—CO—, —$R3_2$C—$(CR2_2)_c$—$CR3_2$—, —$R3_2$C—$(CR2_2)_c$—$SO_2$—, —$O_2$S—$(CR2_2)_d$—$SO_2$— or —OC—$(CR2_2)_d$—$SO_2$—, R1 and R3 represent a hydrogen group, an alkyl group, a halogen group, or a halogenated alkyl group and are respectively identical or different, but at least one of R1 and R3 is respectively a halogen group or a halogenated alkyl group; R2 represents a hydrogen group, an alkyl group, a halogen group, or a halogenated alkyl group, and are identical or different; a, f, and n represent an integer number of 1 or 2; b and d represent one of integer numbers 1 to 4; c represents 0 or one of integer numbers 1 to 4; and e and m represent one of integer numbers 1 to 3.

According to an embodiment, there is provided an electrochemical device including an electrolytic solution, wherein the electrolytic solution contains a solvent and an electrolyte salt, and the electrolyte salt contains an ionic compound having a structure shown in Chemical formula 1.

Chemical formula 1

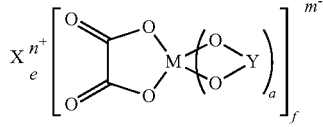

where $X^{n+}$ represents an ion of a Group 1A element or a Group 2A element in the short period periodic table, or an onium ion; M represents a transition metal, or a Group 3B element, a Group 4B element or a Group 5B element in the short period periodic table; Y represents —OC—$(CR1_2)_b$—CO—, —$R3_2$C—$(CR2_2)_c$—CO—, —$R3_2$C—$(CR2_2)_c$—$CR3_2$—, —$R3_2$C—$(CR2_2)_c$—$SO_2$—, —$O_2$S—$(CR2_2)_d$—$SO_2$— or —OC—$(CR2_2)_d$—$SO_2$—; R1 and R3 represent a hydrogen group, an alkyl group, a halogen group, or a halogenated alkyl group and are respectively identical or different, but at least one of R1 and R3 is respectively a halogen group or a halogenated alkyl group; R2 represents a hydrogen group, an alkyl group, a halogen group, or a halogenated alkyl group, and are identical or different; a, f, and n represent an integer number of 1 or 2; b and d represent one of integer numbers 1 to 4; c represents 0 or one of integer numbers 1 to 4; and e and m represent one of integer numbers 1 to 3.

According to an embodiment, there is provided a battery including a cathode, an anode, and an electrolytic solution, wherein the electrolytic solution contains a solvent and an electrolyte salt, and the electrolyte salt contains an ionic compound having a structure shown in Chemical formula 1.

Chemical formula 1

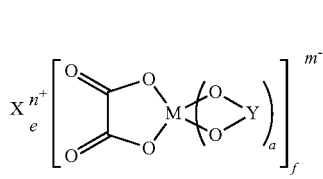

where $X^{n+}$ represents an ion of a Group 1A element or a Group 2A element in the short period periodic table, or an onium ion; M represents a transition metal, or a Group 3B element, a Group 4B element or a Group 5B element in the short period periodic table; Y represents —OC—$(CR1_2)_b$—CO—, —$R3_2$C—$(CR2_2)_c$—CO—, —$R3_2$C—$(CR2_2)_c$—$CR3_2$—, —$R3_2$C—$(CR2_2)_c$—$SO_2$—, —$O_2$S—$(CR2_2)_d$—$SO_2$— or —OC—$(CR2_2)_d$—$SO_2$—; R1 and R3 represent a hydrogen group, an alkyl group, a halogen group, or a halogenated alkyl group and are respectively identical or different, but at least one of R1 and R3 is respectively a halogen group or a halogenated alkyl group; R2 represents a hydrogen group, an alkyl group, a halogen group, or a halogenated alkyl group, and are identical or different; a, f, and n represent an integer number of 1 or 2; b and d represent one of integer numbers 1 to 4; c represents 0 or one of integer numbers 1 to 4; and e and m represent one of integer numbers 1 to 3.

The ionic compound of the embodiment has the structure shown in Chemical formula 1. Therefore, the solubility and the chemical stability can be improved. Therefore, according to the electrolytic solution of the embodiment using the ionic compound, the chemical stability can be improved. According to the electrochemical device and the battery of the embodiments using the electrolytic solution, the cycle characteristics can be improved.

Additional features and advantages are described herein, and will be apparent from, the following Detailed Description and the figures.

DETAILED DESCRIPTION

Figure 1:
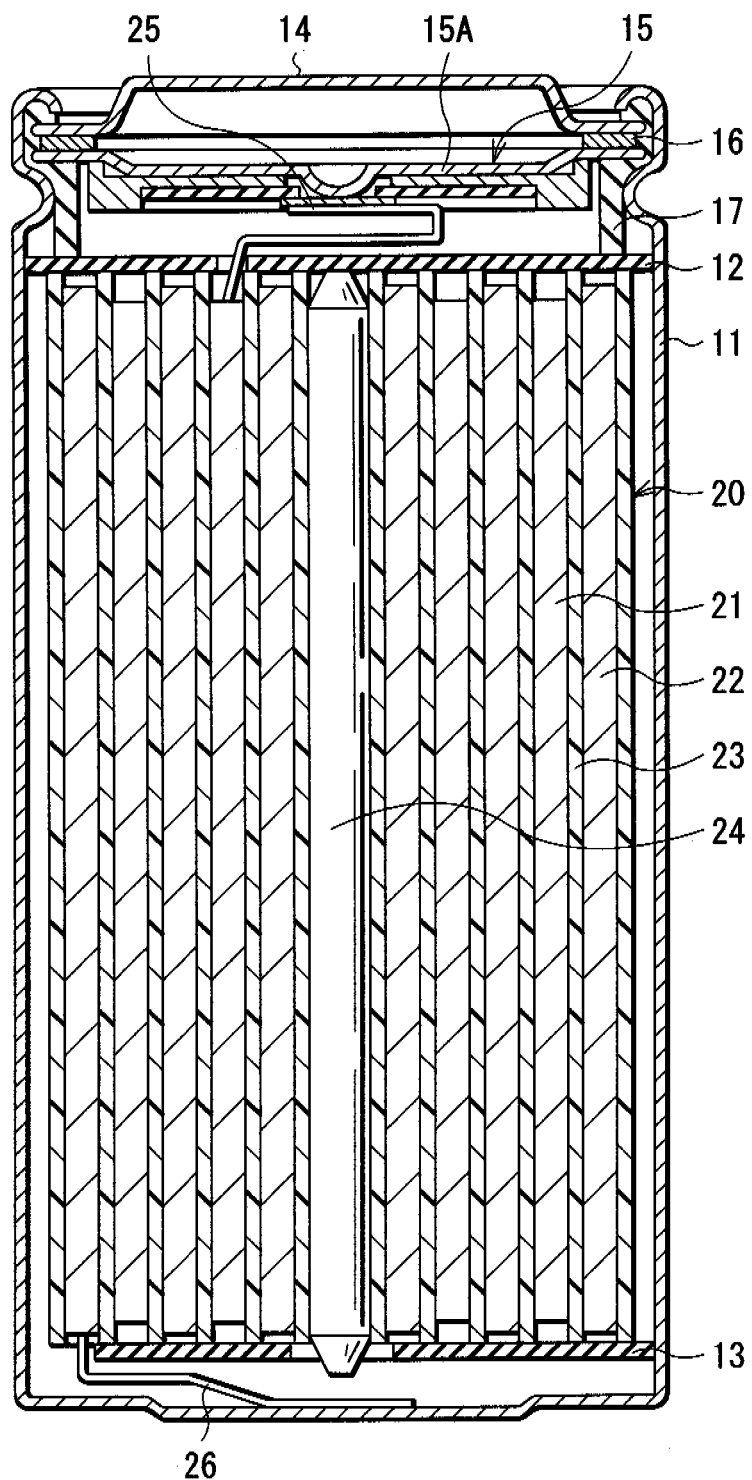
FIG. 1 is a cross section showing a structure of a first battery using an ionic compound according to an embodiment as an electrolyte salt.

An embodiment will be hereinafter described in detail with reference to the drawings.

An ionic compound according to an embodiment has a structure shown in Chemical formula 1. In an anion of the ionic compound, two different types of ligands, that is, an oxalic acid ligand (—O—OC—CO—O—) and a ligand having an oxygen chelate structure (—O—Y—O—) are introduced to a central element (M). As the central element, for example, boron is preferable, since thereby sufficient solubility and chemical stability can be obtained.

Chemical formula 1

In the formula, $X^{n+}$ represents an ion of a Group 1A element or a Group 2A element in the short period periodic table, or an onium ion. M represents a transition metal; or a Group 3B element, a Group 4B element, or a Group 5B element in the short period periodic table. Y represents —OC—$(CR1_2)_b$—CO—, —$R3_2$C—$(CR2_2)_c$—CO—, —$R3_2$C—$(CR2_2)_c$—$CR3_2$—, —$R3_2$C—$(CR2_2)_c$—$SO_2$—, —$O_2$S—$(CR2_2)_d$—$SO_2$—, or —OC—$(CR2_2)_d$—$SO_2$—. R1 and R3 represent a hydrogen group, an alkyl group, a halogen group, or a halogenated alkyl group and may be respectively identical or different, but at least one of them is respectively a halogen group or a halogenated alkyl group. R2 represents a hydrogen group, an alkyl group, a halogen group, or a halogenated alkyl group, and may be identical or different. a, f, and n represent an integer number of 1 or 2. b and d represent one of integer numbers 1 to 4. c represents 0 or one of integer numbers 1 to 4. e and m represent one of integer numbers 1 to 3.

A description will be hereinafter given of examples of the ionic compound by categorizing the compounds according to the type of a cation.

Ionic compounds containing a lithium ion ($Li^+$) as a representative of the ion of the Group 1A element or the Group 2A element include compounds shown in Chemical formulas 2 and 3, that is, (2,2-difluoromalonate oxalate)lithium borate in Chemical formula 2(1), [(2,2-bistrifluoromethyl)malonate oxalate]lithium borate in Chemical formula 2(2), [bis(3,3,3-trifluoromethyl)glycolate oxalate]lithium borate in Chemical formula 2(3), (2-trifluoromethylpropionate oxalate)lithium borate in Chemical formula 2(4), (3,3,3-trifluoromethylpropionate oxalate)lithium borate in Chemical formula 2(5), (difluoroaceto oxalate)lithium borate in Chemical formula 2(6), (2,3,3,3-tetrafluoropropionate oxalate)lithium borate in Chemical formula 2(7), and (methanedisulfonate oxalate) lithium borate in Chemical formula 2(8) and the like; and (difluoromethanedisulfonate oxalate)lithium borate in Chemical formula 3(1), (sulfoaceto oxalate)lithium borate in Chemical formula 3(2), (difluorosulfoaceto oxalate)lithium borate in Chemical formula 3(3), (4,4,4-trifluoro-3-trifluoromethyl butylate oxalate)lithium borate in Chemical formula 3(4), (perfluoropinacolate oxalate)lithium borate in Chemical formula 3(5), (3-trifluoromethyl butylate oxalate) lithium borate in Chemical formula 3(6), (4,4,4-trifluoro butylate oxalate)lithium borate in Chemical formula 3(7) and the like. Specially, (2,2-difluoromalonate oxalate)lithium borate, [bis(3,3,3-trifluoromethyl)glycolate oxalate]lithium borate, (2-trifluoromethylpropionate oxalate)lithium borate, or (3,3,3-trifluoromethylpropionate oxalate)lithium borate is preferable, since thereby sufficient effects can be obtained.

Chemical formula 2

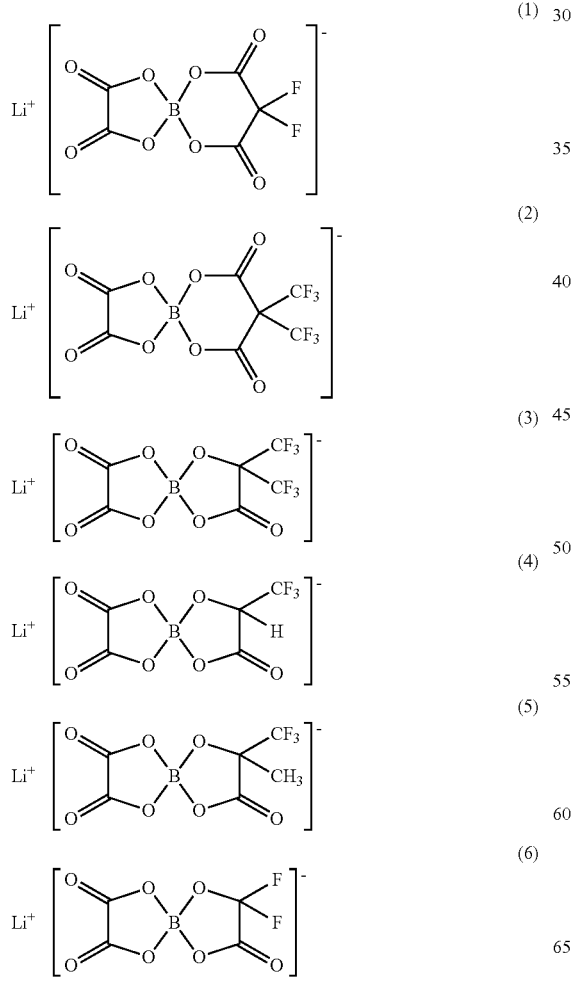

Chemical formula 3

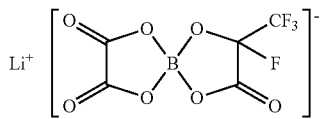

(7)

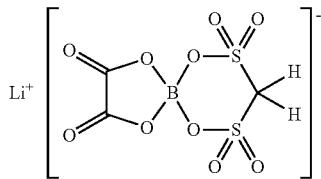

(8)

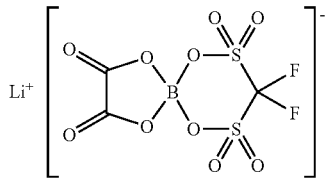

(1)

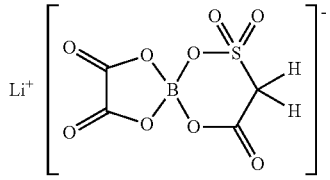

(2)

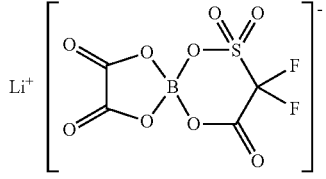

(3)

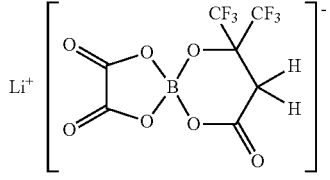

(4)

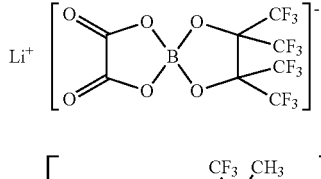

(5)

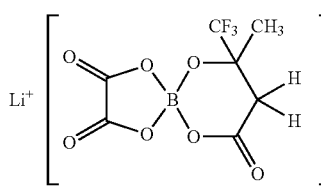

(6)

(7)

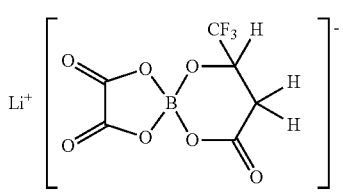

Ionic compounds containing a tetraethylammonium ion (($C_2H_5)_4N^+$) as a representative of the onium ion include compounds shown in Chemical formulas 4 and 5, that is, (2,2-difluoromalonate oxalate)tetraethylammonium borate in Chemical formula 4(1), [(2,2-bistrifluoromethyl)malonate oxalate]tetraethylammonium borate in Chemical formula 4(2), [bis(3,3,3-trifluoromethyl)glycolate oxalate]tetraethylammonium borate in Chemical formula 4(3), (2-trifluoromethylpropionate oxalate)tetraethylammonium borate in Chemical formula 4(4), (3,3,3-trifluoromethylpropionate oxalate)tetraethylammonium borate in Chemical formula 4(5), (difluoroaceto oxalate)tetraethylammonium borate in Chemical formula 4(6), (2,3,3,3-tetrafluoropropionate oxalate)tetraethylammonium borate in Chemical formula 4(7), (methanedisulfonate oxalate)tetraethylammonium borate in Chemical formula 4(8) and the like; and (difluoromethanedisulfonate oxalate)tetraethylammonium borate in Chemical formula 5(1), (sulfoaceto oxalate)tetraethylammonium borate in Chemical formula 5(2), (difluoroaceto oxalate)tetraethylammonium borate in Chemical formula 5(3), (4,4,4-trifluoro-3-trifluoromethyl butylate oxalate)tetraethylammonium borate in Chemical formula 5(4), (perfluoropinacolate oxalate)tetraethylammonium borate in Chemical formula 5(5), (3-trifluoromethyl butylate oxalate)tetraethylammonium borate in Chemical formula 5(6), (4,4,4-trifluoro butylate oxalate)tetraethylammonium borate in Chemical formula 5(7) and the like.

Chemical formula 4

(1)

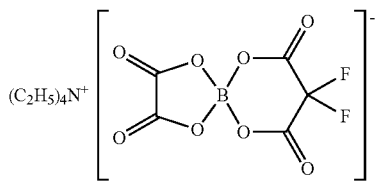

(2)

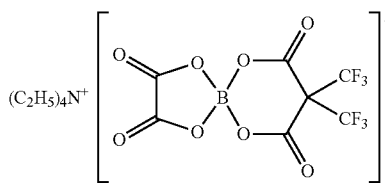

(3)

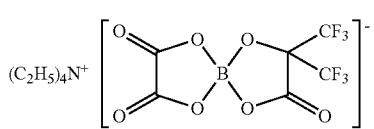

(4)

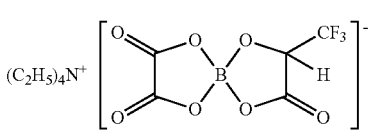

(5)

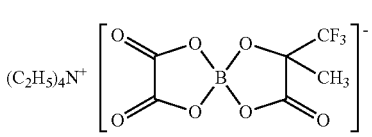

(6)

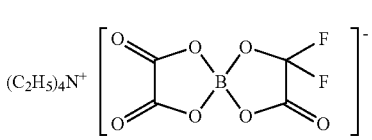

(7)

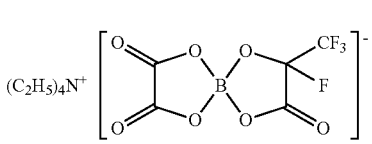

(8)

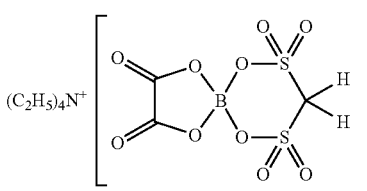

Chemical formula 5

(1)

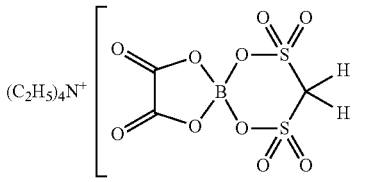

(2)

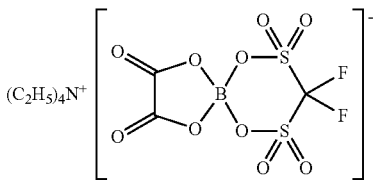

(3)

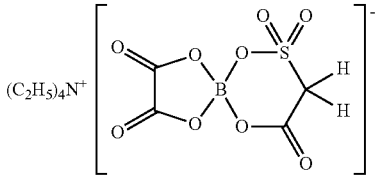

(4)

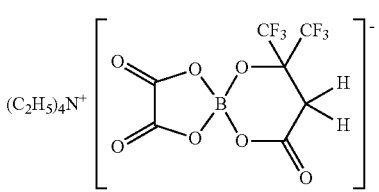

-continued

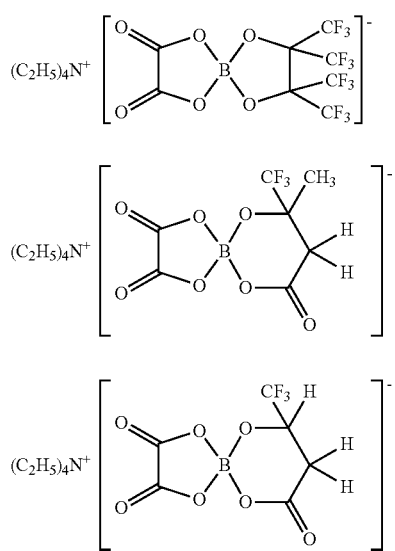

Ionic compounds containing a triethylmethylammonium ion (($C_2H_5$)$_3$NCH$_3^+$) include compounds shown in Chemical formulas 6 and 7, that is, (2,2-difluoromalonate oxalate)triethylmethylammonium borate in Chemical formula 6(1), [(2,2-bistrifluoromethyl)malonate oxalate]triethylmethylammonium borate in Chemical formula 6(2), [bis(3,3,3-trifluoromethyl)glycolate oxalate]triethylmethylammonium borate in Chemical formula 6(3), (2-trifluoromethylpropionate oxalate)triethylmethylammonium borate in Chemical formula 6(4), (3,3,3-trifluoromethylpropionate oxalate)triethylmethylammonium borate in Chemical formula 6(5), (difluoroaceto oxalate)triethylmethylammonium borate in Chemical formula 6(6), (2,3,3,3-tetrafluoropropionate oxalate)triethylmethylammonium borate in Chemical formula 6(7), and (methanedisulfonate oxalate)triethylmethylammonium borate in Chemical formula 6(8) and the like; and (difluoromethanedisulfonate oxalate)triethylmethylammonium borate in Chemical formula 7(1), (sulfoaceto oxalate)triethylmethylammonium borate in Chemical formula 7(2), (difluorosulfoaceto oxalate)triethylmethylammonium borate in Chemical formula 7(3), (4,4,4-trifluoro-3-trifluoromethyl butylate oxalate)triethylmethylammonium borate in Chemical formula 7(4), (perfluoropinacolate oxalate)triethylmethylammonium borate in Chemical formula 7(5), (3-trifluoromethyl butylate oxalate)triethylmethylammonium borate in Chemical formula 7(6), (4,4,4-trifluoro butylate oxalate)triethylmethylammonium borate in Chemical formula 7(7) and the like.

Chemical formula 6

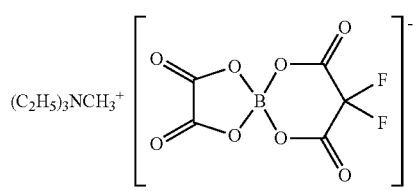

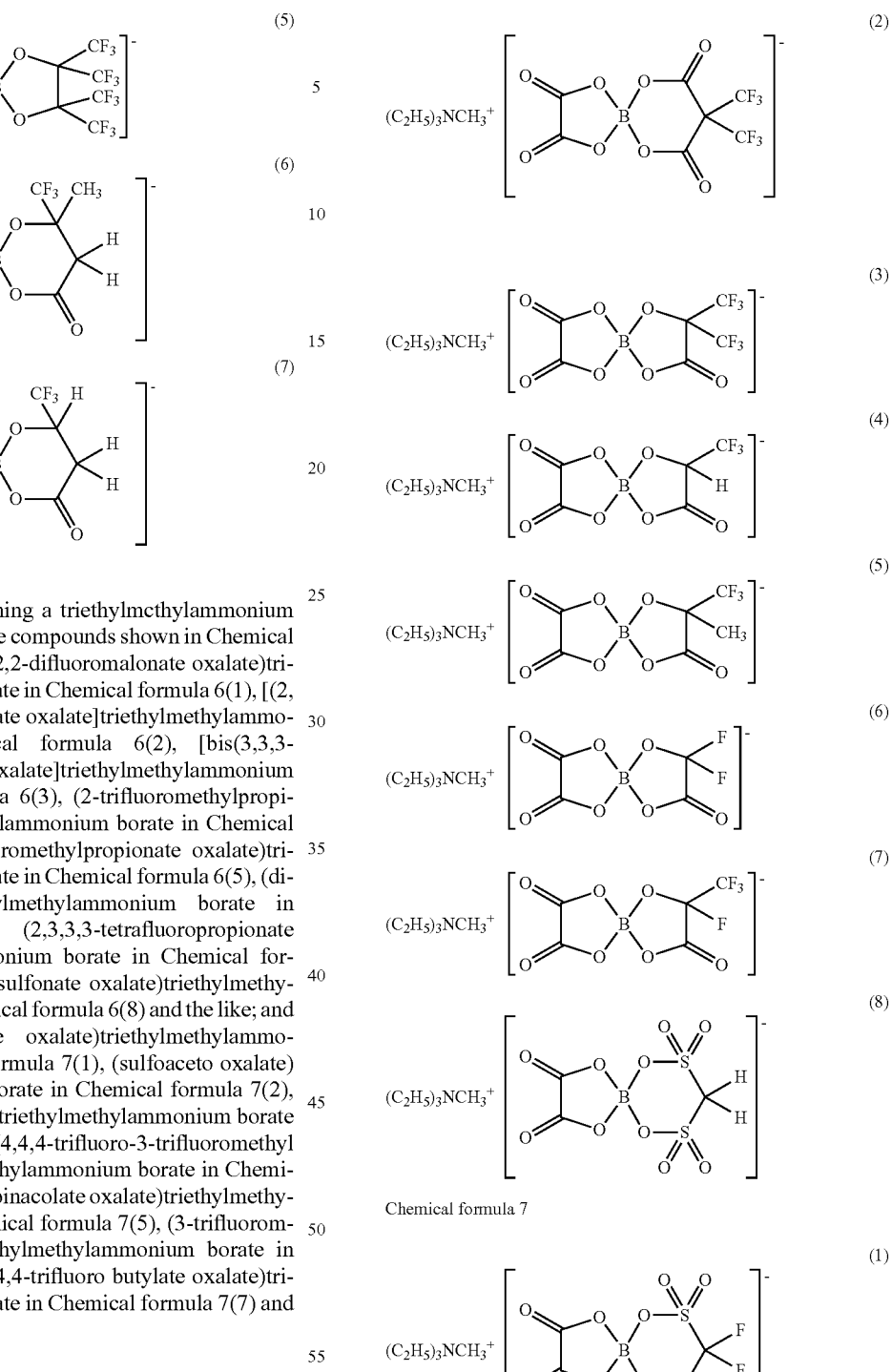

Chemical formula 7

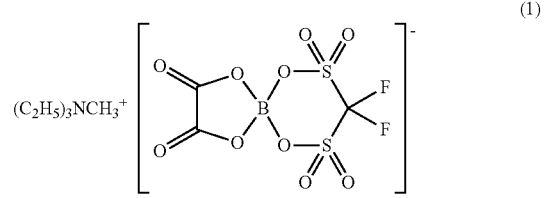

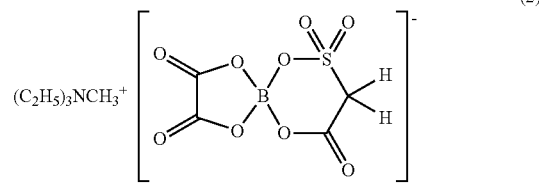

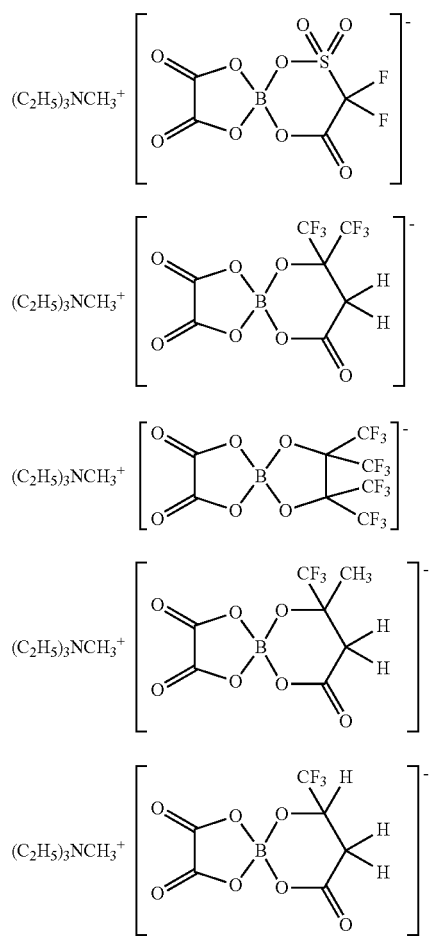

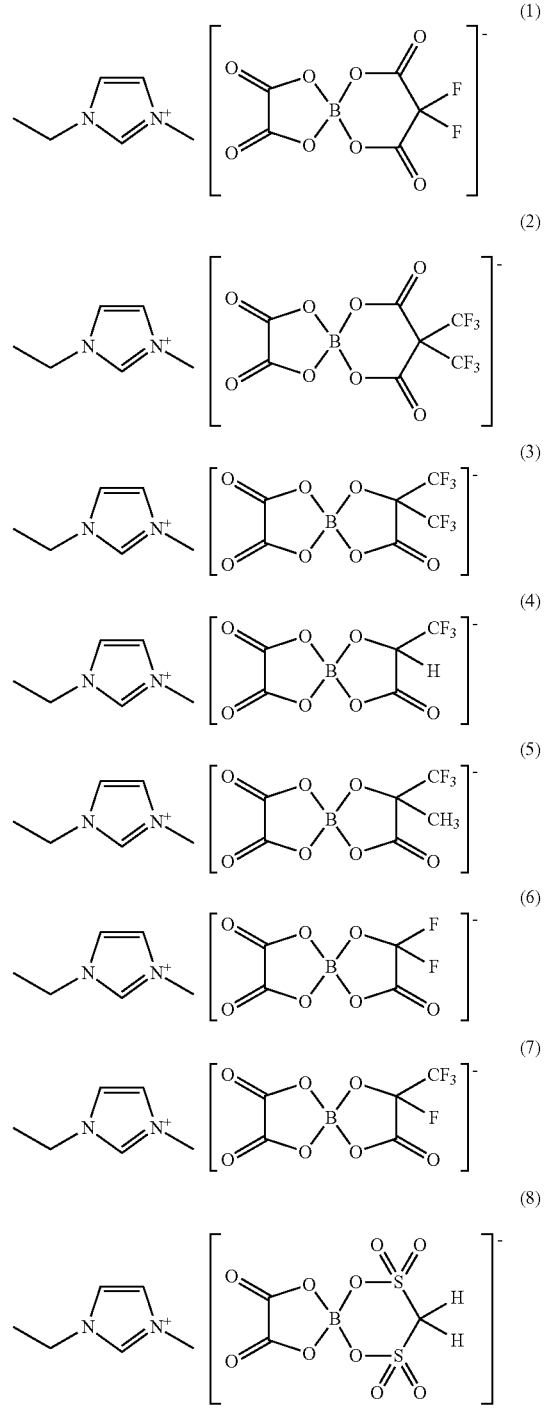

Chemical formula 8

Chemical formula 9

Ionic compounds containing an ethylmethylimidazolium ion ($C_6H_{11}N_2^+$) include compounds shown in Chemical formulas 8 and 9, that is, (2,2-difluoromalonate oxalate)ethylmethylimidazolium borate in Chemical formula 8(1), [(2,2-bistrifluoromethyl)malonate oxalate] ethylmethylimidazolium borate in Chemical formula 8(2), [bis(3,3,3-trifluoromethyl)glycolate oxalate]ethylmethylimidazolium borate in Chemical formula 8(3), (2-trifluoromethylpropionate oxalate)ethylmethylimidazolium borate in Chemical formula 8(4), (3,3,3-trifluoromethylpropionate oxalate)ethylmethylimidazolium borate in Chemical formula 8(5), (difluoroaceto oxalate)ethylmethylimidazolium borate in Chemical formula 8(6), (2,3,3,3-tetrafluoropropionate oxalate)ethylmethylimidazolium borate in Chemical formula 8(7), and (methanedisulfonate oxalate)ethylmethylimidazolium borate in Chemical formula 8(8) and the like; and (difluoromethanedisulfonate oxalate)ethylmethylimidazolium borate in Chemical formula 9(1), (sulfoaceto oxalate)ethylmethylimidazolium borate in Chemical formula 9(2), (difluorosulfoaceto oxalate)ethylmethylimidazolium borate in Chemical formula 9(3), (4,4,4-trifluoro-3-trifluoromethyl butylate oxalate)ethylmethylimidazolium borate in Chemical formula 9(4), (perfluoropinacolate oxalate)ethylmethylimidazolium borate in Chemical formula 9(5), (3-trifluoromethyl butylate oxalate)ethylmethylimidazolium borate in Chemical formula 9(6), (4,4,4-trifluoro butylate oxalate)ethylmethylimidazolium borate in Chemical formula 9(7) and the like.

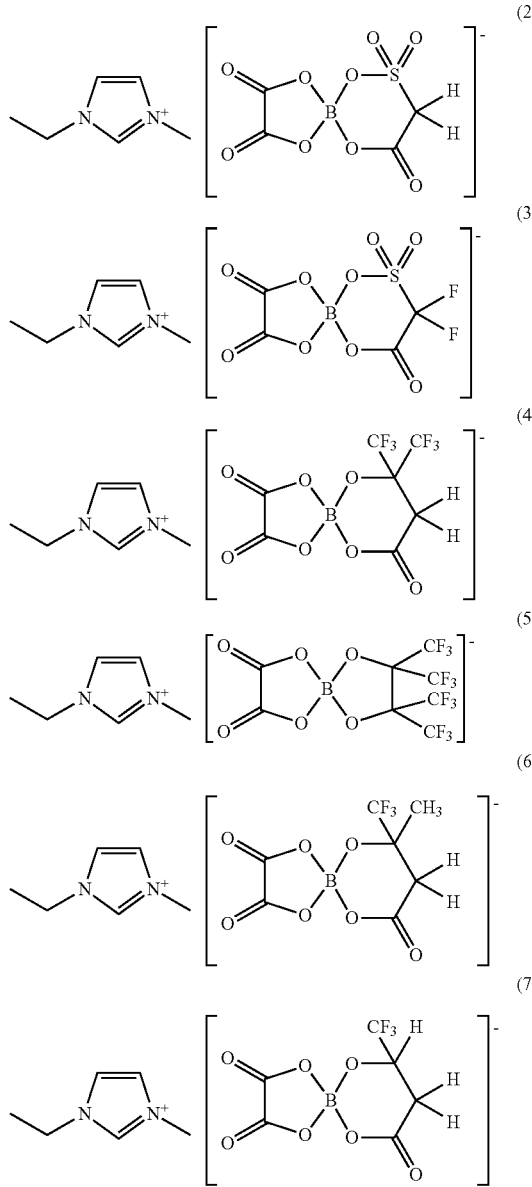

It is needless to say that the ionic compound according to this embodiment is not limited to the compounds shown in Chemical formula 2 to Chemical formula 9, and the ionic compounds according to this embodiment include any compound having the structure shown in Chemical formula 1. Though not described in detail, as a cation, for example, an ammonium ion ($NH_4^+$), a phosphonium ion ($PH_4^+$) and the like can be also cited in addition to the foregoing cations.

In the ionic compound, the anion has an asymmetric structure in which two different types of ligands are introduced to the central element. In addition, the ligand having the oxygen chelate structure in the anion has a halogen as an element. In this case, compared to a compound with the anion having a symmetric structure such as bis(oxalate)lithium borate shown in Chemical formula 10, or a compound in which the anion has an asymmetric structure but the ligand having an oxygen chelate structure does not have a halogen as an element such as (malonate oxalate)lithium borate shown in Chemical formula 11, the following advantages can be obtained. Firstly, since the anion has the asymmetric structure, electronic deflection is generated in the vicinity of the central element, and thereby the dissociation property is improved. Secondly, since the ligand having the oxygen chelate structure has a halogen as an element, the dissociation property is further improved due to the high electron absorption characteristics of the halogen. Thirdly, since the ligand having the oxygen chelate structure has the large three-dimensional size (three-dimensional protective effect), the central element is hardly reacted, that is, the decomposition is prevented.

Chemical formula 10

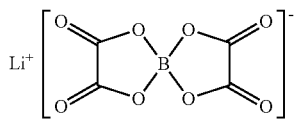

Chemical formula 11

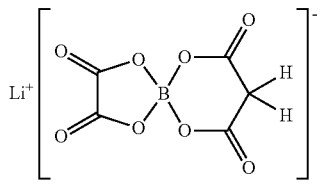

The ionic compound may be used as a simple substance, or may be used by being mixed with other material. Usage application of the ionic compound can be voluntarily set according to the cation type. As an example, in the case of the ionic compound containing an asymmetric ammonium ion such as the triethylmethyl ammonium ion or an imidazolium ion, the simple substance thereof can be directly used as an ionic liquid. The ionic compound containing the lithium ion, the ammonium ion, the phosphonium ion or the like can be used as an electrolyte salt composing an electrolytic solution for an electrochemical device. In particular, the ionic compound containing the lithium ion is suitable for a secondary battery and the like. The ionic compound containing the ammonium ion and the ionic compound containing the phosphonium ion are suitable for an electric double-layer capacitor and the like.

The ionic compound of this embodiment has the structure shown in Chemical formula 1. Thus, as described above, the dissociation property is improved and the decomposition is prevented. Therefore, the solubility and the chemical stability can be improved.

Next, a description will be given of a usage example of the ionic compound according to this embodiment. Taking a secondary battery including an electrolytic solution as an electrochemical device, the ionic compound is used for the secondary battery as follows.

First Battery

FIG. 1 shows a cross sectional structure of a first battery using the ionic compound as an electrolyte salt. The battery is a lithium ion secondary battery in which the anode capacity is expressed by the capacity component based on insertion and extraction of lithium as an electrode reactant. FIG. 1 shows a battery structure of a so-called cylinder type secondary battery.

The secondary battery contains a spirally wound electrode body 20 in which a cathode 21 and an anode 22 are spirally wound with a separator 23 in between, and a pair of insulating plates 12 and 13 inside a battery can 11 in the shape of an approximately hollow cylinder. The battery can 11 is made of, for example, iron (Fe) plated by nickel (Ni). One end of the battery can 11 is closed, and the other end thereof is opened.

The pair of insulating plates 12 and 13 is arranged to sandwich the spirally wound electrode body 20 in between and to extend perpendicularly to the spirally wound periphery face.

At the open end of the battery can 11, a battery cover 14, and a safety valve mechanism 15 and a PTC (Positive Temperature Coefficient) device 16 provided inside the battery cover 14 are attached by being caulked with a gasket 17. Inside of the battery can 11 is thereby hermetically sealed. The battery cover 14 is made of, for example, a material similar to that of the battery can 11. The safety valve mechanism 15 is electrically connected to the battery cover 14 through the PTC device 16. In the safety valve mechanism 15, when the internal pressure of the battery becomes a certain level or more by internal short circuit, external heating or the like, a disk plate 15A flips to cut the electric connection between the battery cover 14 and the spirally wound electrode body 20. When temperature rises, the PTC device 16 increases the resistance and thereby limits a current to prevent abnormal heat generation resulting from a large current. The gasket 17 is made of, for example, an insulating material and its surface is coated with asphalt.

For example, a center pin 24 is inserted in the center of the spirally wound electrode body 20. In the spirally wound electrode body 20, a cathode lead 25 made of aluminum (Al) or the like is connected to the cathode 21, and an anode lead 26 made of nickel or the like is connected to the anode 22. The cathode lead 25 is electrically connected to the battery cover 14 by being welded to the safety valve mechanism 15. The anode lead 26 is welded and thereby electrically connected to the battery can 11.

Figure 2:
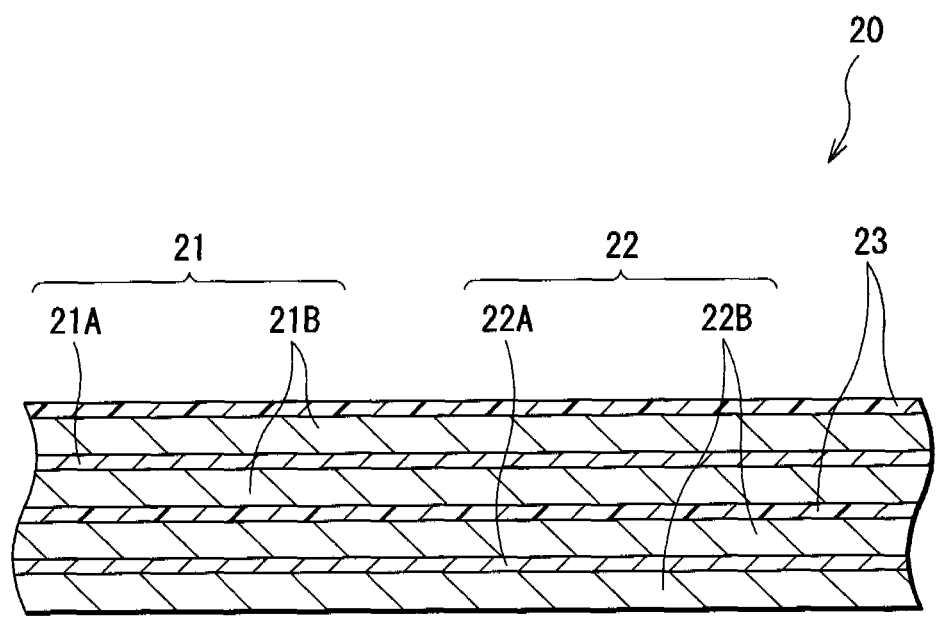
FIG. 2 is a cross section showing an enlarged part of a spirally wound electrode body shown in FIG. 1.

FIG. 2 shows an enlarged part of the spirally wound electrode body 20 shown in FIG. 1. The cathode 21 has a structure in which, for example, a cathode active material layer 21B is provided on the both faces of a cathode current collector 21A having a pair of opposed faces. The cathode current collector 21A is made of, for example, a metal material such as aluminum, nickel, and stainless. The cathode active material layer 21B contains, for example, as a cathode active material, one or more cathode materials capable of inserting and extracting lithium as an electrode reactant. If necessary, the cathode active material layer 21B may contain an electrical conductor, a binder and the like.

As the cathode material capable of inserting and extracting lithium, for example, a lithium complex oxide such as lithium cobalt oxide, lithium nickel oxide, a solid solution containing them ($Li(Ni_xCo_yMn_z)O_2$, values of x, y, and z are respectively expressed as $0<x<1$, $0<y<1$, $0<z<1$, and $x+y+z=1$), lithium manganese oxide having a spinel structure ($LiMn_2O_4$), and a solid solution thereof ($Li(Mn_{2-v}Ni_v)O_4$, a value of v is expressed as $v<2$); or a phosphate compound having an olivine structure such as lithium iron phosphate ($LiFePO_4$) is preferable. Thereby, a high energy density can be obtained. In addition to the foregoing, for example, an oxide such as titanium oxide, vanadium oxide, and manganese dioxide; a disulfide such as iron disulfide, titanium disulfide, and molybdenum sulfide; sulfur; a conductive polymer compound such as polyaniline and polythiophene can be cited.

The anode 22 has a structure in which, for example, an anode active material layer 22B is provided on the both faces of an anode current collector 22A having a pair of opposed faces. The anode current collector 22A is made of, for example, a metal material such as copper (Cu), nickel, and stainless. The anode active material layer 22B contains, for example, as an anode active material, one or more anode materials capable of inserting and extracting lithium. If necessary, the anode active material layer 22B may contain an electrical conductor, a binder and the like.

As the anode material capable of inserting and extracting lithium, for example, a carbon material can be cited. As the carbon material, for example, graphitizable carbon, non-graphitizable carbon in which the spacing of (002) plane is 0.37 nm or more, or graphite in which the spacing of (002) plane is 0.34 nm or less can be cited. More specifically, pyrolytic carbons, coke, graphite, glassy carbons, an organic polymer compound fired body, carbon fiber, activated carbon, carbon black or the like can be cited. Of the foregoing, the coke includes pitch coke, needle coke, petroleum coke and the like. The organic polymer compound fired body is obtained by firing and carbonizing a phenol resin, a furan resin or the like at an appropriate temperature. In the carbon material, a change in the crystal structure due to insertion and extraction of lithium is very little. Therefore, for example, by using the carbon material together with the other anode material, a high energy density can be obtained and superior cycle characteristics can be obtained. In addition, the carbon material also functions as an electrical conductor, and thus the carbon material is preferably used.

In addition, as the anode material capable of inserting and extracting lithium, for example, a material that is capable of inserting and extracting lithium, and contains at least one of metal elements and metalloid elements as an element can be cited. Such an anode material is preferably used, since a high energy density can be thereby obtained. Such an anode material may be a simple substance, an alloy, or a compound of a metal element or a metalloid element, or may have one or more phases thereof at least in part. In the invention, alloys include an alloy containing one or more metal elements and one or more metalloid elements, in addition to an alloy including two or more metal elements. Further, an alloy in the invention may contain a nonmetallic element. The texture thereof includes a solid solution, a eutectic crystal (eutectic mixture), an intermetallic compound, and a texture in which two or more thereof coexist.

As such a metal element or such a metalloid element composing the anode material, for example, a metal element or a metalloid element capable of forming an alloy with lithium can be cited. Specifically, magnesium (Mg), boron (B), aluminum, gallium (Ga), indium (In), silicon (Si), germanium (Ge), tin (Sn), lead (Pb), bismuth (Bi), cadmium (Cd), silver (Ag), zinc (Zn), hafnium (Hf), zirconium (Zr), yttrium (Y), palladium (Pd), platinum (Pt) and the like can be cited. Of the foregoing, at least one of silicon and tin is particularly preferable. Silicon and tin have the high ability to insert and extract lithium, and can provide a high energy density.

As an anode material containing at least one of silicon and tin, for example, the simple substance, an alloy, or a compound of silicon; the simple substance, an alloy, or a compound of tin; or a material having one or more phases thereof at least in part can be cited. As the alloy of silicon, for example, an alloy containing at least one selected from the group consisting of tin, nickel, copper, iron, cobalt, manganese, zinc, indium, silver, titanium, germanium, bismuth, antimony, and chromium as a second element other than silicon can be cited. As the alloy of tin, for example, an alloy containing at least one selected from the group consisting of silicon, nickel, copper, iron, cobalt (Co), manganese (Mn), zinc, indium, silver, titanium (Ti), germanium, bismuth, antimony (Sb), and chromium (Cr) as a second element other than tin can be cited.

As the compound of silicon or the compound of tin, for example, a compound containing oxygen (O) or carbon (C)

can be cited. In addition to silicon or tin, the compound may contain the foregoing second element.

In particular, as the anode material containing at least one of silicon and tin, for example, an anode material containing a second element and a third element in addition to tin as a first element is also preferable. As the second element, at least one selected from the group consisting of cobalt, iron, magnesium, titanium, vanadium (V), chromium, manganese, nickel, copper, zinc, gallium, zirconium, niobium (Nb), molybdenum (Mo), silver, indium, cerium (Ce), hafnium, tantalum (Ta), tungsten (W), bismuth, and silicon is used. As the third element, at least one selected from the group consisting of boron, carbon, aluminum, and phosphorus is used. When the second element and the third element are contained, the cycle characteristics can be improved.

Specially, as an anode material, a CoSnC-containing material that contains tin, cobalt, and carbon as an element, in which the carbon content is in the range from 9.9 wt % to 29.7 wt %, and the cobalt ratio to the total of tin and cobalt (Co/(Sn+Co)) is in the range from 30 wt % to 70 wt % is preferable. In such a composition range, a high energy density can be obtained, and superior cycle characteristics can be obtained.

The CoSnC-containing material may further contain other element according to needs. As other element, for example, silicon, iron, nickel, chromium, indium, niobium, germanium, titanium, molybdenum, aluminum, phosphorus, gallium, bismuth or the like is preferable. Two or more thereof may be contained, since thereby the capacity or the cycle characteristics can be further improved.

The CoSnC-containing material has a phase containing tin, cobalt, and carbon. Such a phase preferably has a low crystallinity structure or an amorphous structure. Further, in the CoSnC-containing material, at least part of carbon as an element is preferably bonded to a metal element or a metalloid element as other element. It is thought that lowering of cycle characteristics is caused by cohesion or crystallization of tin or the like. In this regard, when carbon is bonded to other element, such cohesion or crystallization can be prevented.

As a measurement method for examining bonding state of elements, for example, X-ray Photoelectron Spectroscopy (XPS) can be cited. In XPS, in the case of graphite, the peak of is orbit of carbon (C1s) is observed at 284.5 eV in the apparatus in which energy calibration is made so that the peak of 4f orbit of gold atom (Au4f) is obtained in 84.0 eV. In the case of surface contamination carbon, the peak is observed at 284.8 eV. Meanwhile, in the case of higher electric charge density of carbon element, for example, when carbon is bonded to a metal element or a metalloid element, the peak of C1s is observed in the region lower than 284.5 eV. That is, when the peak of the composite wave of C1s obtained for the CoSnC-containing material is observed in the region lower than 284.5 eV, at least part of carbon contained in the CoSnC-containing material is bonded to the metal element or the metalloid element as other element.

In XPS, for example, the peak of C1s is used for correcting the energy axis of spectrums. Since surface contamination carbon generally exists on the surface, the peak of C1s of the surface contamination carbon is set to in 284.8 eV, which is used as an energy reference. In XPS, the waveform of the peak of C1s is obtained as a form including the peak of the surface contamination carbon and the peak of carbon in the CoSnC-containing material. Therefore, the waveform of C1s is analyzed by, for example, commercially available software to separate the peak of the surface contamination carbon and the peak of carbon in the CoSnC-containing material. In the analysis of the waveform, the position of the main peak existing on the lowest bound energy side is set to the energy reference (284.8 eV).

As the anode material capable of inserting and extracting lithium, for example, a metal oxide, a polymer compound and the like capable of inserting and extracting lithium can be cited. As the metal oxide, for example, iron oxide, ruthenium oxide, molybdenum oxide or the like can be cited. As the polymer compound, for example, polyaniline, polypyrrole or the like can be cited.

As the electrical conductor, for example, a carbon material such as graphite, carbon black, and Ketjen black can be cited. Such a carbon material may be used singly, or two or more thereof may be used by mixing. The electrical conductor may be a metal material, a conductive polymer or the like as long as the material has the electric conductivity.

As the binder, for example, a synthetic rubber such as styrene-butadiene rubber, fluorinated rubber, and ethylene propylene diene; or a polymer material such as polyvinylidene fluoride can be cited. One thereof may be used singly, or two or more thereof may be used by mixing. However, when the cathode 21 and the anode 22 are spirally wound as shown in FIG. 1, flexible styrene-butadiene rubber, flexible fluorinated rubber or the like is preferably used.

In the secondary battery, by adjusting the amount of the cathode active material and the amount of the anode material, the charge capacity of the anode material becomes larger than the charge capacity of the cathode active material, so that lithium metal is not precipitated on the anode 22 even when fully charged.

The separator 23 separates the cathode 21 from the anode 22, and passes lithium ions while preventing current short circuit due to contact of the both electrodes. The separator 23 is made of, for example, a porous film made of a synthetic resin such as polytetrafluoroethylene, polypropylene, and polyethylene, or a ceramics porous film. The separator 23 may have a structure in which two or more porous films as the foregoing porous films are layered. Specially, a polyolefin porous film is preferable since the polyolefin porous film has superior effects for preventing short circuit, and can contribute to improve battery safety by the shutdown effect. In particular, polyethylene is preferable since the shutdown effect can be obtained in the range from 100 deg C. to 160 deg C., and their electrochemical stability is superior. Polypropylene is also preferable. In addition, as long as a resin has the chemical stability, the resin may be used by being copolymerized or blended with polyethylene or polypropylene.

An electrolytic solution as a liquid electrolyte is impregnated in the separator 23. The electrolytic solution contains a liquid solvent, for example, a nonaqueous solvent such as an organic solvent and an electrolyte salt dissolved therein.

As the nonaqueous solvent, for example, ethylene carbonate, propylene carbonate, butylene carbonate, dimethyl carbonate, diethyl carbonate, ethyl methyl carbonate, methyl propyl carbonate, γ-butyrolactone, γ-valerolactone, 1,2-dimethoxyethane, tetrahydrofuran, 2-methyl-tetrahydrofuran, tetrahydropyran, 1,3-dioxolane, 4-methyl-1,3-dioxolane, 1,3-dioxane, 1,4-dioxane, methyl acetate, ethyl acetate, methyl propionate, ethyl propionate, methyl butyrate, methyl isobutyrate, trimethylacetic acid methyl, trimethylacetic acid ethyl, acetonitrile, glutaronitrile, adiponitrile, methoxyacetonitrile, 3-methoxypropionitrile, N,N-dimethylformamide, N-methylpyrrolidinone, N-methyloxazolidinone, N,N'-dimethylimidazolidinone, nitromethane, nitroethane, sulfolane, dimethyl sulfoxide phosphate or the like can be cited. Thereby, superior cycle characteristics can be obtained. One of the foregoing nonaqueous solvents may be used singly, or two or more thereof may be used by mixing. Specially, the solvent preferably contains a mixture of a high-viscosity (high dielectric constant) solvent (for example, dielectric constant ∈≥30) such as ethylene carbonate and propylene carbonate and a low-viscosity solvent (for example, viscosity≤1 mPa·s) such as dimethyl carbonate, ethyl methyl carbonate, and diethyl carbonate. Thereby, the dissociation property of the electrolyte salt and the ion mobility are improved, and thus higher effects can be obtained.

In particular, the solvent preferably contains at least one selected from the group consisting of chain ester carbonate having a halogen as an element shown in Chemical formula 12 and cyclic ester carbonate having a halogen as an element shown in Chemical formula 13. Thereby, higher effects can be obtained.

Chemical formula 12

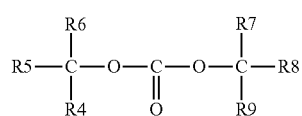

In the formula, R4 to R9 represent a hydrogen group, a halogen group, an alkyl group, or an alkyl halide group. R4 to R9 may be identical or different. However, at least one of R4 to R9 is the halogen group or the alkyl halide group.

Chemical formula 13

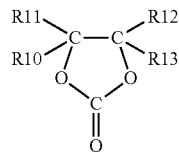

In the formula, R10 to R13 represent a hydrogen group, a halogen group, an alkyl group, or an alkyl halide group. R10 to R13 may be identical or different. However, at least one of R10 to R13 is the halogen group or the alkyl halide group.

As the chain ester carbonate having a halogen as an element shown in Chemical formula 12, for example, fluoromethyl methyl carbonate, bis(fluoromethyl)carbonate, difluoromethyl methyl carbonate or the like can be cited. One thereof may be used singly, or two or more thereof may be used by mixing.

As the cyclic ester carbonate having a halogen as an element shown in Chemical formula 13, for example, compounds shown in Chemical formulas 14 and 15 can be cited. That is, 4-fluoro-1,3-dioxolane-2-one of Chemical formula 14(1), 4-chloro-1,3-dioxolane-2-one of Chemical formula 14(2), 4,5-difluoro-1,3-dioxolane-2-one of Chemical formula 14(3), tetrafluoro-1,3-dioxolane-2-one of Chemical formula 14(4), 4-fluoro-5-chloro-1,3-dioxolane-2-one of Chemical formula 14(5), 4,5-dichloro-1,3-dioxolane-2-one of Chemical formula 14(6), tetrachloro-1,3-dioxolane 2-one of Chemical formula 14(7), 4,5-bistrifluoromethyl-1,3-dioxolane 2-one of Chemical formula 14(8), 4-trifuloromethyl-1,3-dioxolane-2-one of Chemical formula 14(9), 4,5-difluoro-4,5-dimethyl-1,3-dioxolane-2-one of Chemical formula 14(10), 4-methyl-5,5-difluoro-1,3-dioxolane-2-one of Chemical formula 14(11), 4-ethyl-5,5-difluoro-1,3-dioxolane-2-one of Chemical formula 14(12) and the like can be cited. Further, 4-trifluoromethyl-5-fluoro-1,3-dioxolane-2-one of Chemical formula 15(1), 4-trifluoromethyl-5-methyl-1,3-dioxolane-2-one of Chemical formula 15(2), 4-fluoro-4,5-dimethyl-1,3-dioxolane-2-one of Chemical formula 15(3), 4,4-difluoro-5-(1,1-difluoroethyl)-1,3-dioxolane-2-one of Chemical formula 15(4), 4,5-dichloro-4,5-dimethyl-1,3-dioxolane-2-one of Chemical formula 15(5), 4-ethyl-5-fluoro-1,3-dioxolane-2-one of Chemical formula 15(6), 4-ethyl-4,5-difluoro-1,3-dioxolane-2-one of Chemical formula 15(7), 4-ethyl-4,5,5-trifluoro-1,3-dioxolane-2-one of Chemical formula 15(8), 4-fluoro-4-methyl-1,3-dioxolane-2-one of Chemical formula 15(9) and the like can be cited. One thereof may be used singly, or two or more thereof may be used by mixing. Specially, as the cyclic ester carbonate having a halogen as an element, 4-fluoro-1,3-dioxolane-2-one is preferable, and 4,5-difluoro-1,3-dioxolane-2-one is more preferable, since these cyclic ester carbonates are easily available, and can provide higher effects. In particular, as 4,5-difluoro-1,3-dioxolane-2-one, a trans isomer is more preferable than a sis isomer to obtain higher effects.

Chemical formula 14

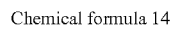

(1)

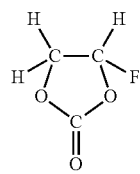

(2)

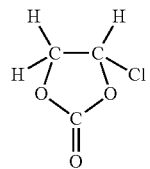

(3)

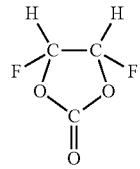

(4)

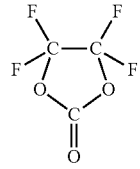

(5)

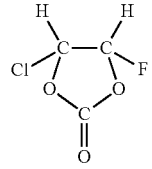

(6)

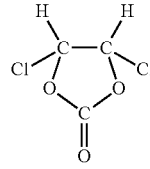

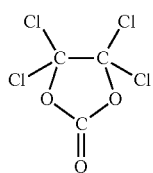
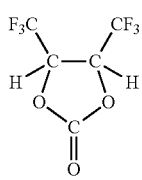
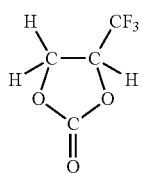
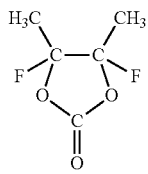
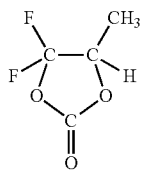
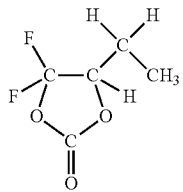

Chemical formula 15

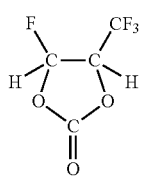

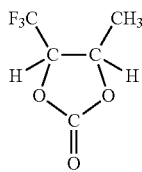

Further, the solvent preferably contains cyclic ester carbonate having an unsaturated bond. Thereby, higher effects can be obtained. As the cyclic ester carbonate having an unsaturated bond, for example, vinylene carbonate, vinyl ethylene carbonate and the like can be cited. One thereof may be used singly, or two or more thereof may be used by mixing. Specially, as the cyclic ester carbonate having an unsaturated bond, vinylene carbonate is preferably included. Thereby, sufficient effects can be obtained. In particular, in the case that the solvent contains the chain ester carbonate having a halogen as an element or the cyclic ester carbonate having a halogen as an element described above, when the solvent further contains the cyclic ester carbonate having an unsaturated bond, significantly high effects can be obtained.

The electrolyte salt contains the foregoing ionic compound. Thereby, the chemical stability of the electrolytic solution is improved, and thus the cycle characteristics can be improved.

The electrolyte salt may contain, for example, one or more light metal salts (excluding the light metal salt corresponding with the ionic compound), in addition to the foregoing ionic compound. Thereby, the electrochemical characteristics of the electrolytic solution can be improved. As the light metal salt, for example, lithium hexafluorophospate ($LiPF_6$), lithium tetrafluoroborate ($LiBF_4$), lithium perchlorate ($LiClO_4$), lithium hexafluoroarsenate ($LiAsF_6$), lithium tetraphenyl borate ($LiB(C_6H_5)_4$), lithium methanesulfonate ($LiCH_3SO_3$), lithium trifluoromethanesulfonate ($LiCF_3SO_3$), lithium tetrachloroaluminate ($LiAlCl_4$), lithium hexafluorosilicate ($Li_2SiF_6$), lithium chloride (LiCl), lithium bromide (LiBr) or the like can be cited. Such a light metal salt may be used singly, or two or more thereof may be used by mixing. Specially, when the electrolyte salt contains lithium hexafluorophospate, the internal resistance is lowered, and thus higher effects can be obtained.

The electrolyte salt may contain the compound shown in Chemical formulas 16 to 18. Thereby, sufficient effects can be obtained. One thereof may be used singly, or two or more thereof may be used by mixing. In particular, for example, the electrolyte salt preferably contains at least one selected from the group consisting of lithium hexafluorophospate, lithium tetrafluoroborate, lithium perchlorate, lithium hexafluoroarsenate, and the compounds shown in Chemical formulas 16 to 18. Thereby, sufficient effects can be obtained.

  Chemical formula 16

In the formula, j and k represent an integer number of 1 or more, and m and n may be identical or different.

Chemical formula 17

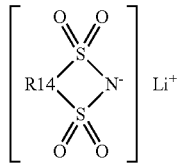

In the formula, R14 represents a straight chain/branched perfluoro alkylene group with the carbon number in the range from 2 to 4.

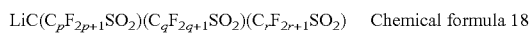  Chemical formula 18

In the formula, p, q, and r represent an integer number of 1 or more, and may be identical or different.

As the chain compound shown in Chemical formula 16, for example, lithium bis(trifluoromethanesulfonyl)imide ($LiN(CF_3SO_2)_2$), lithium bis(pentafluoroethanesulfonyl)imide ($LiN(C_2F_5SO_2)_2$), lithium (trifluoromethanesulfonyl)(pentafluoroethanesulfonyl)imide ($LiN(CF_3SO_2)(C_2F_5SO_2)$), lithium (trifluoromethanesulfonyl)(heptafluoropropanesulfonyl)imide ($LiN(CF_3SO_2)(C_3F_7SO_2)$), lithium (trifluoromethanesulfonyl)(nonafluorobutanesulfonyl)imide ($LiN(CF_3SO_2)(C_4F_9SO_2)$) or the like can be cited.

As the cyclic compound shown in Chemical formula 17, for example, compounds shown in Chemical formula 19 can be cited. That is, lithium 1,2-perfluoroethanedisulfonylimide shown in Chemical formula 19(1), lithium 1,3-perfluoropropanedisulfonylimide shown in Chemical formula 19(2), lithium 1,3-perfluorobutanedisulfonylimide shown in Chemical formula 19(3), lithium 1,4-perfluorobutanedisulfonylimide shown in Chemical formula 19(4) or the like can be cited. One thereof may be used singly, or two or more thereof may be used by mixing. Specially, the electrolyte salt preferably contains lithium 1,3-perfluoropropanedisulfonylimide, since thereby sufficient effects can be obtained.

Chemical formula 19

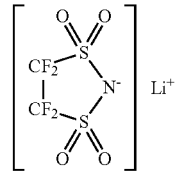 (1)

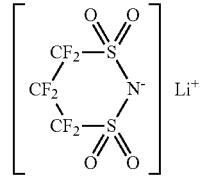 (2)

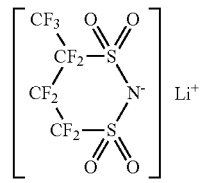 (3)

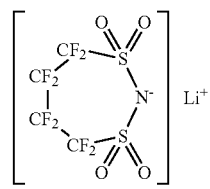 (4)

As the chain compound shown in Chemical formula 18, for example, lithium tris(trifluoromethanesulfonyl)methide ($LiC(CF_3SO_2)_3$) or the like can be cited.

The content of the electrolyte salt in the solvent is preferably in the range from 0.3 mol/kg to 3.0 mol/kg. If the content is out of the foregoing range, there is a possibility that the ion conductivity is significantly lowered and thus it is difficult to obtain sufficient battery characteristics. In particular, when the electrolyte salt contains the light metal salt, the content of the light metal salt is preferably in the range from 0.01 mol/kg to 2.0 mol/kg to the solvent. In such a range, sufficient effects can be obtained.

The secondary battery can be manufactured, for example, as follows.

First, for example, the cathode 21 is formed by forming the cathode active material layer 21B on the both faces of the cathode current collector 21A. The cathode active material layer 21B is formed, as follows. Cathode active material powder, an electrical conductor, and a binder are mixed to prepare a cathode mixture, which is dispersed in a solvent such as N-methyl-2-pyrrolidone to obtain paste cathode mixture slurry. Then, the cathode current collector 21A is coated with the cathode mixture slurry, which is dried, and the resultant is compression-molded. Further, for example, according to a procedure similar to that of the cathode 21, the anode 22 is formed by forming the anode active material layer 22B on the both faces of the anode current collector 22A.

Subsequently, the cathode lead 25 is attached to the cathode current collector 21A by being welded, and the anode lead 26 is attached to the anode current collector 22A by being welded. Subsequently, the cathode 21 and the anode 22 are spirally wound with the separator 23 in between, and thereby the spirally wound electrode body 20 is formed. The end of the cathode lead 25 is welded to the safety valve mechanism 15, and the end of the anode lead 26 is welded to the battery can 11. After that, the spirally wound electrode body 20 is sandwiched between the pair of insulating plates 12 and 13, and contained inside the battery can 11. Subsequently, an electrolytic solution is injected into the battery can 11 and impregnated in the separator 23. Finally, at the open end of the battery can 11, the battery cover 14, the safety valve mechanism 15, and the PTC device 16 are fixed by being caulked with the gasket 17. The secondary battery shown in FIG. 1 and FIG. 2 is thereby completed.

In the secondary battery, when charged, for example, lithium ions are extracted from the cathode 21 and inserted in the anode 22 through the electrolytic solution. Meanwhile, when discharged, for example, lithium ions are extracted from the anode 22, and inserted in the cathode 21 through the electrolytic solution.

According to the secondary battery, in the case that the content of the anode is expressed by the capacity component based on insertion and extraction of lithium, the electrolytic solution contains the foregoing ionic compound as an electrolyte salt. Thus, the chemical stability of the electrolytic solution is improved. Therefore, the cycle characteristics can be improved.

Next, a description will be given of a second battery and a third battery. For the elements common to those of the first battery, the same referential symbols are affixed thereto, and the description thereof will be omitted.

Second Battery

The second battery has a structure, operations, and effects similar to those of the first battery except that the anode 22 has a different structure, and can be manufactured by a procedure similar to that of the first embodiment.

The anode 22 has a structure in which the anode active material layer 22B is provided on the both faces of the anode current collector 22A similarly to in the first battery. The anode active material layer 22B contains an anode active material containing, for example, silicon or tin as an element. Specifically, for example, the anode active material layer 22B contains the simple substance, an alloy, or a compound of silicon, or the simple substance, an alloy, or a compound of tin. The anode active material layer 22B may contain two or more thereof.

The anode active material layer 22B may be formed by using, for example, vapor-phase deposition method, liquid-phase deposition method, spraying method, firing method, or two or more of these methods. The anode active material layer 22B and the anode current collector 22A are preferably alloyed at the interface thereof at least in part. Specifically, it is preferable that at the interface thereof, the element of the anode current collector 22A is diffused in the anode active material layer 22B, or the element of the anode active material layer 22B is diffused in the anode current collector 22A, or both elements are diffused therein each other. Thereby, deconstruction due to expansion and shrinkage of the anode active material layer 22B according to charge and discharge can be prevented, and electron conductivity between the anode active material layer 22B and the anode current collector 22A can be improved.

As vapor-phase deposition method, for example, physical deposition method or chemical deposition method can be cited. Specifically, vacuum vapor deposition method, sputtering method, ion plating method, laser ablation method, thermal CVD (Chemical Vapor Deposition) method, plasma CVD method and the like can be cited. As liquid-phase deposition method, a known technique such as electrolytic plating and electroless plating can be used. Firing method is, for example, a method in which a particulate anode active material, a binder and the like are mixed and dispersed in a solvent, and then the anode current collector 22A is coated with the mixture, and the resultant is heat-treated at a temperature higher than the melting point of the binder and the like. For firing method, a known technique such as atmosphere firing method, reactive firing method, and hot press firing method can be cited.

Third Battery

The third battery is a lithium metal secondary battery in which the capacity of the anode 22 is expressed by the capacity component based on precipitation and dissolution of lithium. The secondary battery has a structure similar to that of the first battery, except that the anode active material layer 22B is made of a lithium metal, and is manufactured in the same manner as that of the first battery.

In the secondary battery, the lithium metal is used as an anode active material. Thereby, a high energy density can be obtained. The anode active material layer 22B may exist in assembling. Otherwise, it is possible that the anode active material layer 22B does not exist in assembling, and is made of the lithium metal precipitated in charging. Otherwise, by using the anode active material layer 22B as a current collector, the anode current collector 22A may be omitted.

In the secondary battery, when charged, for example, lithium ions are extracted from the cathode 21, and precipitated as the lithium metal on the surface of the anode current collector 22A through the electrolytic solution. Meanwhile, when discharged, for example, the lithium metal is eluted as lithium ions from the anode active material layer 22B, and the lithium ion are inserted in the cathode 21 through the electrolytic solution.

According to this secondary battery, in the case that the capacity of the anode is expressed by the capacity component based on precipitation and dissolution of lithium, the electrolytic solution contains the foregoing ionic compound as an electrolyte salt. Therefore, the cycle characteristics can be improved.

Fourth Battery

Figure 3:
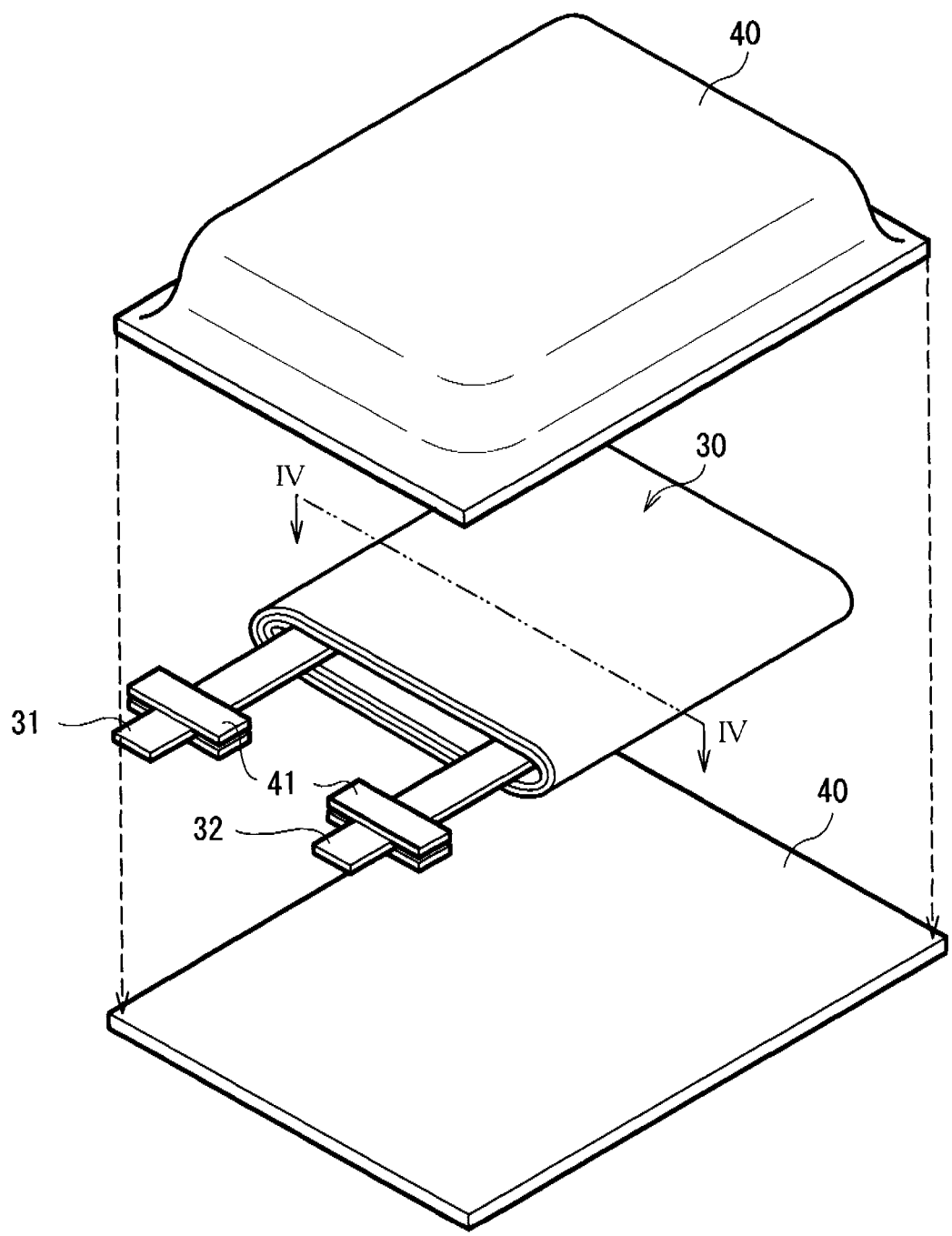
FIG. 3 is an exploded perspective view showing a structure of a forth battery using the ionic compound according to the embodiment as an electrolyte salt.

FIG. 3 shows an exploded perspective structure of a fourth battery. In the battery, a spirally wound electrode body 30 on which a cathode lead 31 and an anode lead 32 are attached is contained inside a film package member 40. The battery structure is a so-called laminated type secondary battery.

The cathode lead 31 and the anode lead 32 are respectively directed from inside to outside of the package member 40 in the same direction, for example. The cathode lead 31 is made of, for example, a metal material such as aluminum. The anode lead 32 is made of, for example, a metal material such as copper, nickel, and stainless. The respective metal materials composing the cathode lead 31 and the anode lead 32 are in the shape of a thin plate or mesh.

The package member 40 is made of a rectangular aluminum laminated film in which, for example, a nylon film, an aluminum foil, and a polyethylene film are bonded together in this order. The package member 40 is, for example, arranged so that the polyethylene film and the spirally wound electrode body 30 are opposed, and the respective outer edges are contacted to each other by fusion bonding or an adhesive. An adhesive film 41 to protect from entering of outside air is inserted between the package member 40 and the cathode lead 31, the anode lead 32. The adhesive film 41 is made of a material having contact characteristics to the cathode lead 31 and the anode lead 32, for example, is made of a polyolefin resin such as polyethylene, polypropylene, modified polyethylene, and modified polypropylene.

The package member 40 may be made of a laminated film having other structure, a polymer film such as polypropylene, or a metal film, instead of the foregoing three-layer aluminum laminated film.

Figure 4:
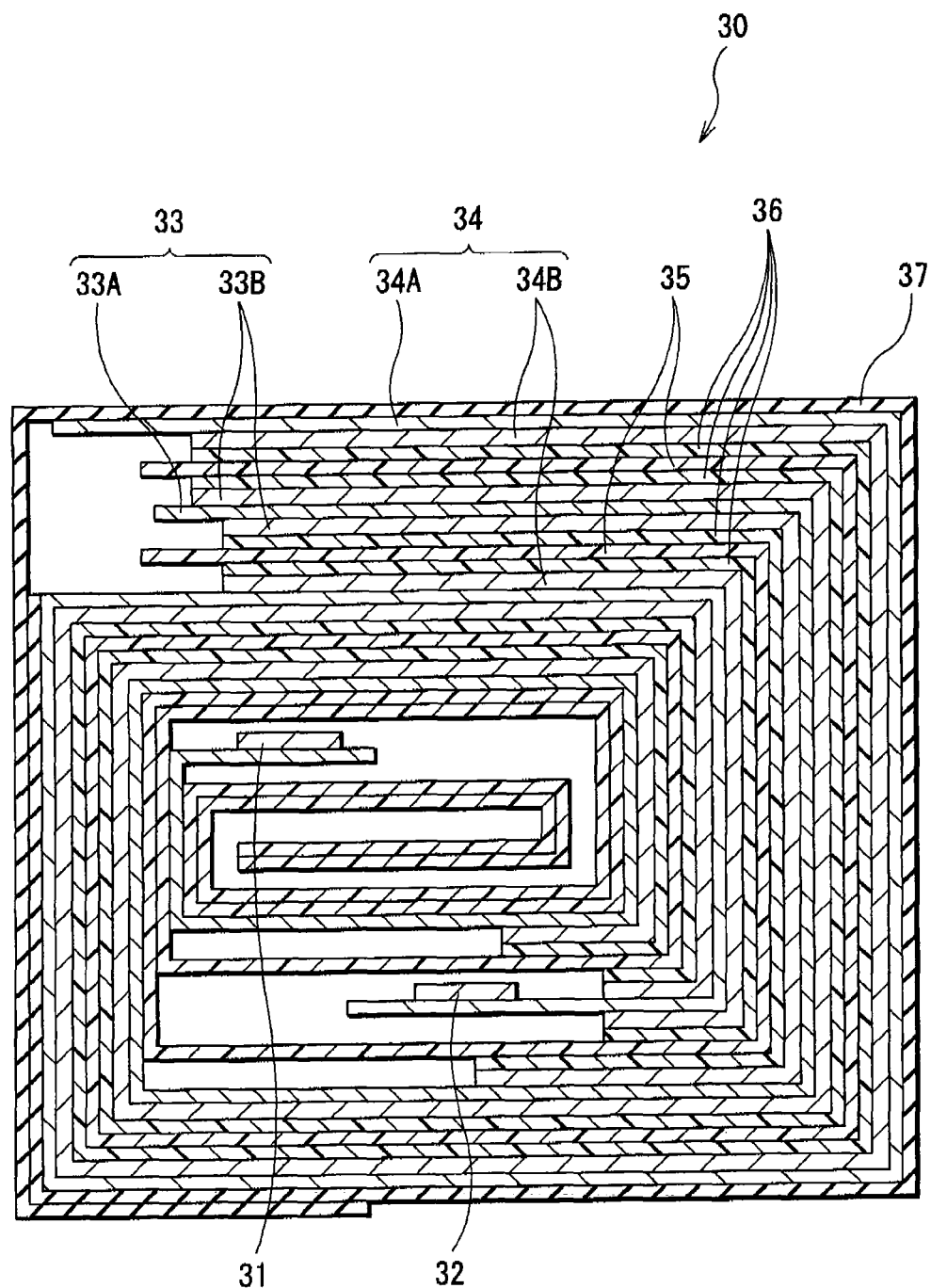
FIG. 4 is a cross section showing a structure taken along line IV-IV of a spirally wound electrode body shown in FIG. 3.

FIG. 4 shows a cross sectional structure taken along line IV-IV of the spirally wound electrode body 30 shown in FIG. 3. In the spirally wound electrode body 30, a cathode 33 and an anode 34 are layered with a separator 35 and an electrolyte 36 in between and then spirally wound. The outermost periphery thereof is protected by a protective tape 37.

The cathode 33 has a structure in which a cathode active material layer 33B is provided on the both faces of a cathode current collector 33A. The anode 34 has a structure in which an anode active material layer 34B is provided on the both faces of an anode current collector 34A. Arrangement is made so that the anode active material layer 34B faces the cathode active material layer 33B. The structures of the cathode current collector 33A, the cathode active material layer 33B, the anode current collector 34A, the anode active material layer 34B, and the separator 35 are similar to those of the cathode current collector 21A, the cathode active material layer 21B, the anode current collector 22A, the anode active material layer 22B, and the separator 23 of the first battery and the second battery.

The electrolyte 36 is so-called gelatinous, containing an electrolytic solution that contains the foregoing ionic compound as an electrolyte salt and a polymer compound that holds the electrolytic solution. The gel electrolyte is preferable, since high ion conductivity (for example, 1 mS/cm or more at high temperature) can be obtained and liquid leakage of the battery can be prevented.

As the polymer compound, for example, polyacrylonitrile, polyvinylidene fluoride, a copolymer of polyvinylidene fluoride and polyhexafluoropropylene, polytetrafluoroethylene, polyhexafluoropropylene, polyethylene oxide, polypropylene oxide, polyphosphazene, polysiloxane, polyvinyl acetate, polyvinyl alcohol, polymethylmethacrylate, polyacrylic acid, polymethacrylic acid, styrene-butadiene rubber, nitrile-butadiene rubber, polystyrene, polycarbonate or the like can be cited. One of these polymer compounds may be used singly, or two or more thereof may be used by mixing. In particular, in terms of electrochemical stability, polyacrylonitrile, polyvinylidene fluoride, polyhexafluoropropylene, polyethylene oxide or the like is preferably used. The addition amount of the polymer compound in the electrolytic solution varies according to the compatibility thereof, and for example, is preferably in the range from 5 wt % to 50 wt %.

The content of the electrolyte salt is similar to that of the first to the third batteries. However, in this case, the solvent means a wide concept including not only the liquid solvent but also a solvent having ion conductivity capable of dissociating the electrolyte salt. Therefore, when the polymer compound having ion conductivity is used, the polymer compound is also included in the solvent.

As the electrolyte 36, instead of the electrolyte in which the electrolytic solution is held by the polymer compound, the electrolytic solution may be directly used. In this case, the electrolytic solution is impregnated in the separator 35.

The secondary battery is manufactured, for example, as follows.

First, a precursor solution containing an electrolytic solution, a polymer compound, and a mixed solvent is prepared. Then, the cathode 33 and the anode 34 are respectively coated with the precursor solution. After that, the mixed solvent is volatilized to form the electrolyte 36. Subsequently, the cathode lead 31 is attached to the cathode current collector 33A, and the anode lead 32 is attached to the anode current collector 34A. Subsequently, the cathode 33 and the anode 34 formed with the electrolyte 36 are layered with the separator 35 in between to obtain a lamination. After that, the lamination is spirally wound in the longitudinal direction, the protective tape 37 is adhered to the outermost periphery thereof to form the spirally wound electrode body 30. Subsequently, for example, the spirally wound electrode body 30 is sandwiched between the package members 40, and outer edges of the package members 40 are contacted by thermal fusion bonding or the like to enclose the spirally wound electrode body 30. At this time, the adhesive film 41 is inserted between the cathode lead 31/the anode lead 32 and the package member 40. Thereby, the secondary battery shown in FIG. 3 and FIG. 4 is completed.

Otherwise, the secondary battery may be manufactured as follows. First, the cathode lead 31 and the anode lead 32 are respectively attached on the cathode 33 and the anode 34. After that, the cathode 33 and the anode 34 are layered with the separator 35 in between and spirally wound. The protective tape 37 is adhered to the outermost periphery thereof, and a spirally wound body as a precursor of the spirally wound electrode body 30 is formed. Subsequently, the spirally wound body is sandwiched between the package members 40, the peripheral edges except one side are thermally fusion-bonded to obtain a pouched state, and the spirally wound body is contained inside the pouched-like package member 40. Subsequently, a composition of matter for electrolyte containing an electrolytic solution, a monomer as a raw material for a polymer compound, a polymerization initiator, and if necessary other material such as a polymerization inhibitor is prepared, which is injected into the pouched-like package member 40. After that, the opening of the package member 40 is hermetically sealed by, for example, thermal fusion bonding or the like. Finally, the monomer is thermally polymerized to obtain a polymer compound. Thereby, the gel electrolyte 36 is formed. Consequently, the secondary battery shown in FIG. 3 and FIG. 4 is completed.

The operations and the effects of the secondary battery are similar to those of the first or the second batteries described above.

EXAMPLES

Specific examples of the invention will be described in detail.

First, as a representative of the ionic compound of the invention, 6 types of compounds shown in Chemical formulas 2(1), 2(3), 2(4), 2(5), 3(4) and 3(5) were synthesized. After that, the compounds were identified by a nuclear magnetic resonance (NMR) with the use of acetone-$d_6$ as a deuteration solvent.

(2,2-difluoromalonate oxalate)lithium borate shown in Chemical formula 2(1) was synthesized by the following procedure. That is, 25 g of (difluoro oxalate)lithium borate coordinated with ethyl methyl carbonate (EMC), 4.88 g of 2,2-difluoromalonate, and 60 cm$^3$ of dimethyl carbonate (DMC) were mixed. 3.26 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 3.2 g of a colorless compound was obtained. The compound was identified by the NMR. In the result, 11B-NMR spectrum (reference: $NaBH_4$) was observed at 3.54 ppm (quin.), and 19F-NMR spectrum (reference: $CF_3COOH$) was observed at −112.6842 ppm (m), −112.7698 ppm (m), and −113.0145 ppm (m). Accordingly, it was confirmed that the obtained compound was (2,2-difluoromalonate oxalate)lithium borate.

[bis(3,3,3-trifluoromethyl)glycolate oxalate]lithium borate shown in Chemical formula 2(3) was synthesized by the following procedure. That is, 12 g of difluoro[bis(3,3,3-trifluoromethyl)glycolate]lithium borate coordinated with EMC, 4.88 g of 2,2-difluoromalonate, and 60 cm³ of DMC were mixed. 3.26 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 3.2 g of a colorless compound was obtained. The compound was identified by the NMR. In the result, 11B-NMR spectrum (reference: $NaBH_4$) was observed at 7.9049 ppm (quin.), and 19F-NMR spectrum (reference: $CF_3COOH$) was observed at −76.1016 ppm (m) and −76.1505 ppm (m). Accordingly, it was confirmed that the obtained compound was [bis(3,3,3-trifluoromethyl)glycolate oxalate]lithium borate.

(2-trifluoromethylpropionate oxalate)lithium borate shown in Chemical formula 2(4) was synthesized by the following procedure. That is, 72.12 g of (difluoro oxalate) lithium borate coordinated with EMC, 15.86 g of 2-hidroxy-2-(trifluoromethyl)propionic acid, and 60 cm³ of DMC were mixed. 9.37 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 12.5 g of a colorless compound was obtained. The compound was identified by the NMR. In the result, 1H-NMR spectrum was observed at 1.4655 ppm, 1.4637 ppm, and 1.4618 ppm, 11B-NMR spectrum (reference: $NaBH_4$) was observed at 7.5841 ppm (quin.), and 19F-NMR spectrum (reference: $CF_3COOH$) was observed at −80.5551 ppm (m), −80.6041 ppm (m), and −80.9834 ppm (m). Accordingly, it was confirmed that the obtained compound was (2-trifluoromethylpropionate oxalate)lithium borate.

(3,3,3-trifluoromethylpropionate oxalate)lithium borate shown in Chemical formula 2(5) was synthesized by the following procedure. That is, 79.37 g of (difluoro oxalate) lithium borate coordinated with EMC, 15.91 g of 2-hidroxy-3,3,3-trifluoropropionic acid, and 60 cm³ of DMC were mixed. 10.32 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 12.2 g of a colorless compound was obtained. The compound was identified by the NMR. In the result, 1H-NMR spectrum was observed at 4.7371 ppm and 4.7215 ppm, 11B-NMR spectrum (reference: $NaBH_4$) was observed at 8.111 ppm (quin.), and 19F-NMR spectrum (reference: $CF_3COOH$) was observed at −77.0926 ppm (m). Accordingly, it was confirmed that the obtained compound was (3,3,3-trifluoromethylpropionate oxalate)lithium borate.

(4,4,4-trifluoro-3-trifluoromethyl butylate oxalate)lithium borate shown in Chemical formula 3(4) was synthesized by the following procedure. That is, 62.8 g of (difluoro oxalate) lithium borate coordinated with EMC, 19.73 g of 4,4,4-trifluoro-3-hidroxy-3-trifluoromethyl butylate, and 60 cm³ of DMC were mixed. 8.158 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 23.2 g of a colorless compound was obtained. The compound was identified by the NMR. In the result, 1H-NMR spectrum was observed at 2.8672 ppm, 11B-NMR spectrum (reference: $NaBH_4$) was observed at 4.0021 ppm (quin.), and 19F-NMR spectrum (reference: $CF_3COOH$) was observed at −80.5551 ppm (m), −79.3561 ppm (m), and −79.4050 ppm (m). Accordingly, it was confirmed that the obtained compound was (4,4,4-trifluoro-3-trifluoromethyl butylate oxalate)lithium borate.

(perfluoropinacolate oxalate)lithium borate shown in Chemical formula 3(5) was synthesized by the following procedure. That is, 98.6 g of (difluoro oxalate)lithium borate coordinated with EMC, 45.82 g of hexafluoro-2,3-bistrifluoromethylbutane-2,3-diol, and 60 cm³ of DMC were mixed. 12.82 g of tetrachlorosilane was dropped into the mixture while the mixture was stirred. The mixture was stirred all the night to be reacted. After the reaction, the pressure was decreased to condense the reactant. After that, the reactant was recrystallized with the use of a mixed solvent of acetonitrile and toluene, and thereby 21.5 g of colorless compound was obtained. The compound was identified by the NMR. In the result, 11B-NMR spectrum (reference: $NaBH_4$) was observed at 8.5235 ppm (quin.), and 19F-NMR spectrum (reference: $CF_3COOH$) was observed at −80.5551 ppm (m), −70.1676 ppm (m), and −70.6081 ppm (m). Accordingly, it was confirmed that the obtained compound was (perfluoro pinacolate oxalate)lithium borate.

Based on the foregoing analysis results with the use of the NMR, it was confirmed that the ionic compound according to the invention could be synthesized.

Next, electrolytic solutions were prepared by using the ionic compound as an electrolyte salt.

Examples 1-1 to 1-6

Ethylene carbonate (EC) and DMC were mixed at a volume ratio of 30:70. After that, an electrolyte salt was dissolved into the mixture. As the electrolyte salt, (2,2-difluoromalonate oxalate)lithium borate shown in Chemical formula 2(1) (Example 1-1), [bis(3,3,3-trifluoromethyl)glycolate oxalate]lithium borate shown in Chemical formula 2(3) (Example 1-2), (2-trifluoromethylpropionate oxalate)lithium borate shown in Chemical formula 2(4) (Example 1-3), (3,3,3-trifluoromethylpropionate oxalate)lithium borate shown in Chemical formula 2(5) (Example 1-4), (4,4,4-trifluoro-3-trifluoromethyl butylate oxalate)lithium borate shown in Chemical formula 3(4) (Example 1-5), and (perfluoro pinacolate oxalate)lithium borate shown in Chemical formula 3(5) (Example 1-6) were used.

Examples 2-1 to 2-4

A procedure was performed in the same manner as that of Examples 1-1 to 1-4, except that the mixture ratio (volume ratio) between EC and DMC was changed to 50:50, and the concentration of the electrolyte salt was set to 1 mol/dm$^3$.

Comparative Examples 1-1 and 1-2

A procedure was performed in the same manner as that of Examples 1-1 to 1-4, except that bis(oxalate)lithium borate shown in Chemical formula 10 (Comparative example 1-1) and (malonate oxalate)lithium borate shown in Chemical formula 11 (Comparative example 1-2) were used as an electrolyte salt.

Comparative Example 2

A procedure was performed in the same manner as that of Comparative example 1-1, except that the mixture ratio (volume ratio) between EC and DMC was changed to 50:50, and the concentration of the electrolyte salt was set to 0.6 mol/dm$^3$.

For the electrolytic solutions of Examples 1-1 to 1-6 and Comparative examples 1-1 and 1-2, the solubility of the electrolyte salt (mol/dm$^3$) was examined, and the results shown in Table 1 were obtained. For the electrolytic solutions of Examples 2-1 to 2-4 and Comparative example 2, the electric conductivity (mS/cm) at 25 deg C. was measured by an AC bipolar cell, and the results shown in Table 2 were obtained.

TABLE 1

| | Electrolyte salt | Solubility (mol/dm$^3$) |
|---|---|---|
| Example 1-1 | Chemical formula 2(1) | >1.0 |
| Example 1-2 | Chemical formula 2(3) | >1.0 |
| Example 1-3 | Chemical formula 2(4) | >1.0 |
| Example 1-4 | Chemical formula 2(5) | >1.0 |
| Example 1-5 | Chemical formula 3(4) | >1.0 |
| Example 1-6 | Chemical formula 3(5) | >1.0 |
| Comparative example 1-1 | Chemical formula 10 | 0.6 |
| Comparative example 1-2 | Chemical formula 11 | 0.05 |

TABLE 2

| | Electrolyte salt | Electric conductivity (mS/cm) |
|---|---|---|
| Example 2-1 | Chemical formula 2(1) | 5.90 |
| Example 2-2 | Chemical formula 2(3) | 6.20 |
| Example 2-3 | Chemical formula 2(4) | 4.77 |
| Example 2-4 | Chemical formula 2(5) | 5.83 |
| Comparative example 2 | Chemical formula 10 | 5.47 |

As shown in Table 1, the solubility of the electrolyte salt (solution amount per unit volume (number of mols) was 0.6 mol/dm$^3$ and 0.05 mol/dm$^3$ respectively in Comparative examples 1-1 and 1-2, that is, under 1.0 mol/dm$^3$. However, in all Examples 1-1 to 1-6, the solubility of the electrolyte salt was over 1.0 mol/dm$^3$. Accordingly, it was confirmed that when the ionic compound of the invention was used, the solubility was improved.

Further, as shown in table 2, the electric conductivity of the electrolytic solution was 5.47 mS/cm in Comparative example 2, and 5.90 mS/cm, 6.20 mS/cm, 4.77 mS/cm, and 5.83 mS/cm in Examples 2-1 to 2-4. That is, the electric conductivity in Examples 2-1, 2-2, and 2-4 was higher than that of Comparative example 2, but the electric conductivity in Example 2-3 was lower than that of Comparative example 2. However, in Example 2-3, the sufficient electric conductivity of 4.5 mS/cm or more was obtained. Accordingly, it was confirmed that when the ionic compound having the structure shown in Chemical formula 1 was contained as an electrolyte salt in the electrolytic solution of the invention, a sufficient electric conductivity was obtained.

Next, as secondary batteries using the electrolytic solution, the cylindrical secondary battery shown in FIG. 1 and FIG. 2 was formed by the following procedure.

1. Carbonaceous Anode

Example 3-1

First, the anode 22 was formed. That is, 50 parts by weight of petroleum pitch as a binder was added to 100 parts by weight of coal coke as filler. The resultant was mixed at 100 deg C., and then the mixture was pressed and compression-molded. Thereby, a precursor of a carbon molded body was obtained. Subsequently, the precursor was provided with heat treatment at under 1000 deg C., and thereby the carbon molded body was obtained. Subsequently, a step in which binder pitch melted at 200 deg C. or less was impregnated in the carbon molded body, and the resultant was provided with heat treatment at 1000 deg C. (pitch impregnation/firing step) was repeated several times. Subsequently, the carbon molded body was provided with heat treatment up to 3000 deg C. in the inert atmosphere, and thereby a graphitizable molded body was obtained. Subsequently, the graphitizable molded body was pulverized to obtain a powder anode active material.

Subsequently, 90 parts by weight of graphite powder as the anode active material and 10 parts by weight of polyvinylidene fluoride as a binder were mixed to obtain an anode mixture. After that, the anode mixture was dispersed in N-methyl-2-pyrrolidone as a solvent and thereby paste anode mixture slurry was obtained. Finally, the both faces of the anode current collector 22A made of a strip-shaped copper foil (being 15 μm thick) were coated with the anode mixture slurry, which was dried. After that, the resultant was compression-molded to obtain the anode active material layer 22B. The area density of the anode active material layer 22B was adjusted to 25 mg/cm$^2$. After that, the anode lead 26 made of nickel was welded to one end of the anode current collector 22A.

Next, the cathode 21 was formed. That is, lithium carbonate ($Li_2CO_3$) and cobalt carbonate ($CoCO_3$) were mixed at a molar ratio of 0.5:1. After that, the mixture was fired in the air at 900 deg C. for 5 hours. Thereby, lithium cobalt complex oxide ($LiCoO_2$) was obtained. The lithium cobalt complex oxide was analyzed by X-ray diffraction method. The result thereof well corresponded to the peak registered in the JCPDS (Joint Committee of Powder Diffraction Standard) file. Subsequently, the lithium cobalt complex oxide was pulverized to obtain a powder cathode active material. Then, the cumulative 50% particle diameter obtained by the laser diffraction method was 15 μm.

Subsequently, 95 parts by weight of lithium cobalt complex oxide and 5 parts by weight of lithium carbonate were mixed. After that, 91 parts by weight of the mixture as a cathode active material, 6 parts by weight of graphite as an electrical conductor, and 3 parts by weight of polyvinylidene fluoride as a binder were mixed to obtain a cathode mixture.

After that, the cathode mixture was dispersed in N-methyl-2-pyrrolidone as a solvent to obtain paste cathode mixture slurry. Finally, the both faces of the cathode current collector 21A made of a strip-shaped aluminum foil (being 20 μm thick) were coated with the cathode mixture slurry, which was dried. After that, the resultant was compression-molded to form the cathode active material layer 21B. The area density of the cathode active material layer 21B was adjusted to 55 mg/cm$^2$. After that, the cathode lead 25 made of aluminum was welded to one end of the cathode current collector 21A.

Subsequently, the cathode 21, the separator 23 made of a micro porous polypropylene film (being 25 μm thick), and the anode 22 were layered in this order. After that, the resultant lamination was spirally wound many times, the end portion of the spirally wound body was fixed by an adhesive tape, and thereby the spirally wound electrode body 20 being 18 mm in outer diameter was formed. Subsequently, the battery can 11 made of iron plated by nickel was prepared. The spirally wound electrode body 20 was sandwiched by the pair of insulating plates 12 and 13, the anode lead 26 was welded to the battery can 11, the cathode lead 25 was welded to the safety valve mechanism 15, and then the spirally wound electrode body 20 was contained inside the battery can 11. Subsequently, the foregoing electrolytic solution of Example 2-1 was injected into the battery can 11 by reduced pressure method.

Subsequently, the battery can 11 was caulked with the gasket 17 coated with asphalt, and thereby, the safety valve mechanism 15, the PTC device 16, and the battery cover 14 were fixed. Thereby, the internal airtightness of the battery can 11 was secured, and the cylindrical secondary battery being 18 mm in diameter and being 65 mm in height was completed.

Examples 3-2 to 3-4

A procedure was performed in the same manner as that of Example 3-1, except that the electrolytic solution of Examples 2-2 to 2-4 was used instead of the electrolytic solution of Example 2-1.

Example 3-5

A procedure was performed in the same manner as that of Example 3-1, except that lithium hexafluorophosphate (LiPF$_6$) was further added as an electrolyte salt, and the concentrations of (2,2-difluoromalonate oxalate)lithium borate shown in Chemical formula 2(1) and lithium hexafluorophospate were respectively 0.2 mol/dm$^3$ and 0.8 mol/dm$^3$.

Example 3-6

A procedure was performed in the same manner as that of Example 3-1, except that lithium hexafluorophosphate (LiPF$_6$) was further added as an electrolyte salt, and the concentrations of [bis(3,3,3-trifluoromethyl)glycolate oxalate]lithium borate shown in Chemical formula 2(3) and lithium hexafluorophospate were respectively 0.2 mol/dm$^3$ and 0.8 mol/dm$^3$.

Example 3-7

A procedure was performed in the same manner as that of Example 3-1, except that lithium hexafluorophosphate and lithium bis(trifluoromethanesulfonyl)imide (LiTFSI) were further added as an electrolyte salt, and the concentrations of (2,2-difluoromalonate oxalate)lithium borate shown in Chemical formula 2(1), lithium hexafluorophospate, and lithium bis(trifluoromethanesulfonyl)imide were respectively 0.1 mol/dm$^3$, 0.8 mol/dm$^3$, and 0.1 mol/dm$^3$.

Example 3-8

A procedure was performed in the same manner as that of Example 3-5, except that EMC was used instead of DEC as a solvent.

Example 3-9

A procedure was performed in the same manner as that of Example 3-5, except that diethyl carbonate (DEC) was used instead of DMC as a solvent.

Example 3-10

A procedure was performed in the same manner as that of Example 3-5, except that vinylene carbonate (VC) as a cyclic ester carbonate having an unsaturated bond was further added as a solvent. The content of VC was set to 2 wt %. "wt %" means the value where the total of the solvent (excluding VC) and the electrolyte salt was 100 wt %. The meaning of "wt %" is similarly used in the following descriptions.

Example 3-11

A procedure was performed in the same manner as that of Example 3-10, except that 4-fluoro-1,3-dioxolane-2-one (FEC) as a cyclic ester carbonate having a halogen as an element was used instead of VC as a solvent.

Example 3-12

A procedure was performed in the same manner as that of Example 3-10, except that 4,5-difluoro-1,3-dioxolane-2-one (DFEC) as a cyclic ester carbonate having a halogen as an element was used instead of VC as a solvent.

Comparative Example 3-1

A procedure was performed in the same manner as that of Example 3-1, except that lithium hexafluorophosphate was used instead of (2,2-difluoromalonate oxalate)lithium borate shown in Chemical formula 2(1) as an electrolyte salt.

Comparative Example 3-2

A procedure was performed in the same manner as that of Example 3-1, except that bis(oxalate)lithium borate shown in Chemical formula 10 was used instead of (2,2-difluoromalonate oxalate)lithium borate shown in Chemical formula 2(1) as an electrolyte salt. The concentration of the electrolyte salt was set so that the solubility of bis(oxalate)lithium borate became the upper limit (0.6 mol/dm$^3$).

Comparative Example 3-3

A procedure was performed in the same manner as that of Example 3-1, except that (malonate oxalate)lithium borate shown in Chemical formula 11 was used instead of (2,2-difluoromalonate oxalate)lithium borate shown in Chemical formula 2(1) as an electrolyte salt. The concentration of the electrolyte salt was set so that the solubility of (malonate oxalate)lithium borate became the upper limit (0.05 mol/dm$^3$).

For the secondary batteries of Examples 3-1 to 3-12 and Comparative examples 3-1 to 3-3, the cycle characteristics were examined. The results shown in Table 3 were obtained. To examine the cycle characteristics, charge and discharge cycle was repeated 100 times, and thereby the discharge capacity retention ratio at the 100th cycle to the discharge capacity at the first cycle, that is, "discharge capacity retention ratio (%)=(discharge capacity at the 100th cycle/discharge capacity at the first cycle)×100 was calculated. The charge and discharge condition of 1 cycle was as follows. That is, charge was performed at the first charge current of 2.75 A (1.25 C) until the charge voltage of 4.1 V. Charge was performed at the second charge current of 1.1 A (0.5 C) until the maximum charge voltage of 4.2 V. Charge was performed at the constant voltage of 4.2 V until the current value became 20 mA. After that, discharge was performed at the discharge current of 2 A until the final voltage of 3.0 V. "C" means the parameter representing a current value in charge and discharge. For example, 1 C means the current value at which the theoretical capacity is completely charged in 1 hour. The procedure, the conditions and the like in examining the foregoing cycle characteristics are similar to those in evaluating the cycle characteristics of the after-mentioned examples and comparative examples.

phospate. In that case, in particular, there was a tendency that the discharge capacity retention ratio was high in the order of Examples 3-4, 3-3, 3-2, and 3-1. It is needless to say that in Examples 3-1 to 3-4 in which since the electrolyte salt had sufficient solubility, the concentration of the electrolyte salt reached 1.0 mol/dm$^3$, the discharge capacity retention ratio was higher than that of Comparative examples 3-2 and 3-3 in which since the electrolyte salt did not have sufficient solubility, the concentration of the electrolyte salt did not reach 1.0 mol/dm$^3$. Accordingly, it was confirmed that in the secondary battery in which the anode 22 contained graphite as an anode active material, when the electrolytic solution contained the ionic compound having the structure shown in Chemical formula 1, the cycle characteristics were improved.

In Examples 3-5 and 3-6 in which lithium hexafluorophospate was added as an electrolyte salt, the discharge capacity retention ratio was higher that that of Examples 3-1 and 3-2, respectively. In Example 3-7 in which lithium hexafluorophospate and lithium bis(trifluoromethanesulfonyl)imide were added together, the discharge capacity retention ratio was still higher than that of Examples 3-5 and 3-6. Accordingly, it was confirmed that in the secondary battery in which the anode 22 contained graphite as an anode active material and the electrolytic solution contained the ionic

TABLE 3

Anode active material: graphite

| | Solvent | Electrolyte salt | | | Discharge capacity retention ratio (%) |
|---|---|---|---|---|---|
| Example 3-1 | EC + DMC | Chemical formula 2(1) 1 mol/dm$^3$ | | | 92 |
| Example 3-2 | | Chemical formula 2(3) 1 mol/dm$^3$ | | | 90 |
| Example 3-3 | | Chemical formula 2(4) 1 mol/dm$^3$ | | | 88 |
| Example 3-4 | | Chemical formula 2(5) 1 mol/dm$^3$ | | | 87 |
| Example 3-5 | | Chemical formula 2(1) 0.2 mol/dm$^3$ | LiPF$_6$ 0.8 mol/dm$^3$ | | 94 |
| Example 3-6 | | Chemical formula 2(3) 0.2 mol/dm$^3$ | | | 93 |
| Example 3-7 | | Chemical formula 2(1) 0.1 mol/dm$^3$ | LiPF$_6$ 0.8 mol/dm$^3$ | LITFSI 0.1 mol/dm$^3$ | 95 |
| Example 3-8 | EC + EMC | Chemical formula 2(1) 0.2 mol/dm$^3$ | LiPF$_6$ 0.8 mol/dm$^3$ | | 94 |
| Example 3-9 | EC + DEC | | | | 93 |
| Example 3-10 | EC + DMC   VC 2 wt % | Chemical formula 2(1) 0.2 mol/dm$^3$ | LiPF$_6$ 0.8 mol/dm$^3$ | | 96 |
| Example 3-11 | FEC 2 wt % | | | | 96 |
| Example 3-12 | DFEC 2 wt % | | | | 96 |
| Comparative example 3-1 | EC + DMC | LiPF$_6$ 1 mol/dm$^3$ | | | 85 |
| Comparative example 3-2 | | Chemical formula 10 0.6 mol/dm$^3$ | | | 80 |
| Comparative example 3-3 | | Chemical formula 11 0.05 mol/dm$^3$ | | | 71 |

As shown in Table 3, in Example 3-1 using (2,2-difluoromalonate oxalate)lithium borate shown in Chemical formula 2(1) as an electrolyte, Example 3-2 using [bis(3,3,3-trifluoromethyl)glycolate oxalate]lithium borate shown in Chemical formula 2(3), Example 3-3 using (2-trifluoromethylpropionate oxalate)lithium borate shown in Chemical formula 2(4), and Example 3-4 using (3,3,3-trifluoromethylpropionate oxalate)lithium borate shown in Chemical formula 2(5), the discharge capacity retention ratio was higher than that of Comparative example 3-1 using lithium hexafluorocompound having the structure shown in Chemical formula 1 as an electrolyte salt, the cycle characteristics were improved even when other light metal salt was added as an electrolyte salt. In this case, it was confirmed that in particular, when lithium hexafluorophosphate and lithium bis(trifluoromethanesulfonyl)imide were added as other electrolyte salt, higher effects were obtained.

In Examples 3-8 and 3-9 respectively using EMC and DEC instead of DMC as a solvent, the discharge capacity retention ratio was almost equal to that of Example 3-5. Accordingly, it was confirmed that in the secondary battery in which the anode 22 contained graphite as an anode active material and the electrolytic solution contained the ionic compound shown in Chemical formula 1 as an electrolyte salt, the cycle characteristics were improved even when the composition of the solvent was changed.

In Examples 3-10 to 3-12 in which VC, FEC, and DFEC were respectively added to the solvent, the discharge capacity retention ratio was higher than that of Example 3-5. Accordingly, it was confirmed that in the secondary battery in which the anode 22 contained graphite as an anode active material and the electrolytic solution contained the ionic compound shown in Chemical formula 1 as an electrolyte salt, the higher effects are obtained when the solvent contained the cyclic ester carbonate having a halogen as an element and the cyclic ester carbonate having an unsaturated bond.

2. Metallic Anode

The cylindrical secondary battery shown in FIG. 1 and FIG. 2 was fabricated by using lithium metal as an anode active material. The secondary battery is a lithium metal secondary battery in which the capacity of the anode 22 is expressed by the capacity component based on precipitation and dissolution of lithium.

Examples 4-1 to 4-4

A procedure was performed in the same manner as that of Examples 3-1 to 3-4, except that the anode active material layer 22B was formed by attaching lithium metal (being 30 μm thick) on the both faces of the anode current collector 22A, instead of coating the both faces of the anode current collector 22A with the anode mixture slurry.

Example 4-5

A procedure was performed in the same manner as that of Example 3-5, except that the concentrations of (2,2-difluoromalonate oxalate)lithium borate in Chemical formula 2(1) and lithium hexafluorophospate were respectively 0.5 mol/$dm^3$ and 0.5 mol/$dm^3$.

Example 4-6

A procedure was performed in the same manner as that of Example 3-6, except that the concentrations of [bis(3,3,3-trifluoromethyl)glycolate oxalate]lithium borate in Chemical formula 2(3) and lithium hexafluorophospate were respectively 0.5 mol/$dm^3$ and 0.5 mol/$dm^3$.

Example 4-7

A procedure was performed in the same manner as that of Example 3-7, except that the concentrations of (2,2-difluoromalonate oxalate)lithium borate shown in Chemical formula 2(1), lithium hexafluorophospate, and lithium bis(trifluoromethanesulfonyl)imide were respectively 0.4 mol/$dm^3$, 0.5 mol/$dm^3$, and 0.1 mol/$dm^3$.

Examples 4-8 to 4-10

A procedure was performed in the same manner as that of Examples 3-10 to 3-12, except that the concentrations of (2,2-difluoromalonate oxalate)lithium borate shown in Chemical formula 2(1) and lithium hexafluorophospate were respectively 0.5 mol/$dm^3$ and 0.5 mol/$dm^3$.

Comparative Examples 4-1 and 4-2

A procedure was performed in the same manner as that of Comparative examples 3-1 and 3-2, except that lithium metal was used instead of graphite as an anode active material.

For the secondary batteries of Examples 4-1 to 4-10 and Comparative examples 4-1 and 4-2, the cycle characteristics were examined. The results shown in Table 4 were obtained.

TABLE 4

Anode active material: lithium metal

| | Solvent | | | Electrolyte salt | | | Discharge capacity retention ratio (%) |
|---|---|---|---|---|---|---|---|
| Example 4-1 | EC + DMC | | | Chemical formula 2(1) 1 mol/$dm^3$ | | | 94 |
| Example 4-2 | | | | Chemical formula 2(3) 1 mol/$dm^3$ | | | 92 |
| Example 4-3 | | | | Chemical formula 2(4) 1 mol/$dm^3$ | | | 90 |
| Example 4-4 | | | | Chemical formula 2(5) 1 mol/$dm^3$ | | | 88 |
| Example 4-5 | | | | Chemical formula 2(1) 0.5 mol/$dm^3$ | $LiPF_6$ 0.5 mol/$dm^3$ | | 95 |
| Example 4-6 | | | | Chemical formula 2(3) 0.5 mol/$dm^3$ | | | 93 |
| Example 4-7 | | | | Chemical formula 2(1) 0.4 mol/$dm^3$ | $LiPF_6$ 0.5 mol/$dm^3$ | LITFSI 0.1 mol/$dm^3$ | 95 |
| Example 4-8 | EC + DMC | VC 2 wt % | | Chemical formula 2(1) 0.5 mol/$dm^3$ | $LiPF_6$ 0.5 mol/$dm^3$ | | 96 |
| Example 4-9 | | FEC 2 wt % | | | | | 96 |
| Example 4-10 | | DFEC 2 wt % | | | | | 96 |
| Comparative example 4-1 | EC + DMC | | | $LiPF_6$ 1 mol/$dm^3$ | | | 20 |

TABLE 4-continued

| | | Anode active material: lithium metal | |
|---|---|---|---|
| | Solvent | Electrolyte salt | Discharge capacity retention ratio (%) |
| Comparative example 4-2 | | Chemical formula 10 0.6 mol/dm$^3$ | 80 |

As shown in Table 4, in Examples 4-1 to 4-4, the discharge capacity retention ratio was higher than that of Comparative example 4-1, and needless to say, higher than that of Comparative example 4-2. In that case, in particular, there was a tendency that the discharge capacity retention ratio was high in the order of Examples 4-4, 4-3, 4-2, and 4-1. Accordingly, it was confirmed that in the secondary battery in which the anode 22 contained lithium metal as an anode active material, when the electrolytic solution contained the ionic compound having the structure shown in Chemical formula 1 as an electrolyte salt, the cycle characteristics were improved.

In Examples 4-5 and 4-6, the discharge capacity retention ratio was higher that that of Examples 4-1 and 4-2, respectively. In Example 4-7, the discharge capacity retention ratio was equal to that of Example 4-5. Accordingly, it was confirmed that in the secondary battery in which the anode 22 contained lithium metal as an anode active material and the electrolytic solution contained the ionic compound shown in Chemical formula 1 as an electrolyte salt, the cycle characteristics were improved even when other light metal salt was added as an electrolyte salt.

In Examples 4-8 to 4-10, the discharge capacity retention ratio was higher than that of Example 4-5. Accordingly, it was confirmed that in the secondary battery in which the anode 22 contained lithium metal as an anode active material and the electrolytic solution contained the ionic compound shown in Chemical formula 1 as an electrolyte salt, the higher effects were obtained when the solvent contained the cyclic ester carbonate having a halogen as an element and the cyclic ester carbonate having an unsaturated bond.

3. Metalloid Anode

The cylindrical secondary battery shown in FIG. 1 and FIG. 2 was fabricated by using silicon as an anode active material. The secondary battery was a lithium ion secondary battery in which the capacity of the anode 22 was expressed by the capacity component based on insertion and extraction of lithium.

Examples 5-1 to 5-6

A procedure was performed in the same manner as that of Examples 3-1 to 3-6, except that the anode active material layer 22B made of silicon was formed on the both faces of the anode current collector 22A by electron beam deposition method.

Example 5-7

A procedure was performed in the same manner as that of Example 3-7, except that the anode active material layer 22B was formed by a procedure similar to that of Examples 5-1 to 5-6, and the concentrations of (2,2-difluoromalonate oxalate) lithium borate shown in Chemical formula 2(1), lithium hexafluorophospate, and lithium bis(trifluoromethanesulfonyl)imide were respectively 0.2 mol/dm$^3$, 0.7 mol/dm$^3$, and 0.1 mol/dm$^3$.

Examples 5-8 to 5-10

A procedure was performed in the same manner as that of Examples 3-10 to 3-12, except that the anode active material layer 22B was formed by a procedure similar to that of Examples 5-1 to 5-6.

Comparative Examples 5-1 and 5-2

A procedure was performed in the same manner as that of Comparative examples 3-1 and 3-2, except that the anode active material layer 22B was formed by a procedure similar to that of Examples 5-1 to 5-6.

For the secondary batteries of Examples 5-1 to 5-10 and Comparative examples 5-1 and 5-2, the cycle characteristics were examined. The results shown in Table 5 were obtained.

TABLE 5

| | Anode active material: silicon | | |
|---|---|---|---|
| | Solvent | Electrolyte salt | Discharge capacity retention ratio (%) |
| Example 5-1 | EC + DMC | Chemical formula 2(1) 1 mol/dm$^3$ | 75 |
| Example 5-2 | | Chemical formula 2(3) 1 mol/dm$^3$ | 74 |
| Example 5-3 | | Chemical formula 2(4) 1 mol/dm$^3$ | 72 |
| Example 5-4 | | Chemical formula 2(5) 1 mol/dm$^3$ | 70 |
| Example 5-5 | | Chemical formula 2(1) 0.2 mol/dm$^3$    LiPF$_6$ 0.8 mol/dm$^3$ | 78 |

TABLE 5-continued

Anode active material: silicon

| | Solvent | | Electrolyte salt | | Discharge capacity retention ratio (%) |
|---|---|---|---|---|---|
| Example 5-6 | | | Chemical formula 2(3) 0.2 mol/dm³ | | 77 |
| Example 5-7 | | | Chemical formula 2(1) 0.2 mol/dm³ | LiPF$_6$ 0.7 mol/dm³    LITFSI 0.1 mol/dm³ | 76 |
| Example 5-8 | EC + DMC | VC 2 wt % | Chemical formula 2(1) 0.2 mol/dm³ | LiPF$_6$ 0.8 mol/dm³ | 80 |
| Example 5-9 | | FEC 2 wt % | | | 78 |
| Example 5-10 | | DFEC 2 wt % | | | 82 |
| Comparative example 5-1 | EC + DMC | | LiPF$_6$ 1 mol/dm³ | | 40 |
| Comparative example 5-2 | | | Chemical formula 10 0.6 mol/dm³ | | 60 |

As shown in Table 5, in Examples 5-1 to 5-4, the discharge capacity retention ratio was higher than that of Comparative example 5-1, and needless to say, higher than that of Comparative example 5-2. In this case, in particular, there was a tendency that the discharge capacity retention ratio was high in the order of Examples 5-4, 5-3, 5-2, and 5-1. Accordingly, it was confirmed that in the secondary battery in which the anode 22 contained silicon as an anode active material, when the electrolytic solution contained the ionic compound having the structure shown in Chemical formula 1 as an electrolyte salt, the cycle characteristics were improved.

In Examples 4-5 and 5-6, the discharge capacity retention ratio was higher that that of Examples 4-1 and 5-2. In Example 5-7, the discharge capacity retention ratio was almost equal to that of Example 5-5. Accordingly, it was confirmed that in the secondary battery in which the anode 22 contained silicon as an anode active material and the electrolytic solution contained the ionic compound shown in Chemical formula 1 as an electrolyte salt, the cycle characteristics were improved even when other light metal salt was added as an electrolyte salt.

In Examples 4-8 to 5-10, the discharge capacity retention ratio was higher than that of Example 5-5. In this case, in particular, in Example 5-10 in which the solvent contained DFEC, the discharge capacity retention ratio was higher than that of Examples 4-8 and 5-9 in which the solvent contained VC and FEC, respectively. Accordingly, it was confirmed that in the secondary battery in which the anode 22 contained silicon as an anode active material and the electrolytic solution contained the ionic compound shown in Chemical formula 1 as an electrolyte salt, the higher effects were obtained when the solvent contained the cyclic ester carbonate having a halogen as an element and the cyclic ester carbonate having an unsaturated bond. In particular, it was confirmed that when the solvent contained DFEC, significant high effects are obtained.

As evidenced by the results of Table 3 to Table 5 described above, it was confirmed that when the electrolytic solution contained the ionic compound having the structure shown in Chemical formula 1 as an electrolyte salt, superior cycle characteristics were obtained compared to the case that the electrolytic solution did not contain the ionic compound regardless of the material used as an anode active material. In particular, when the metalloid material providing a high energy density was used as an anode active material (refer to Table 5), the increase ratio of the discharge capacity retention ratio was largely improved than the case using the material other than the metalloid material (refer to Table 3 and Table 4). Thus, it was found that when the metalloid material was used as an anode active material, higher effects were obtained. When the metalloid material with the high energy density was used as an anode active material, the decomposition reaction of the electrolytic solution in the anode 22 was generated easily compared to the case using a carbon material or the like, and thus the high chemical stability of the ionic compound having the structure shown in Chemical formula 1 was significantly exercised.

The present application has been described with reference to the embodiment and the examples. However, the present application is not limited to the aspects described in the foregoing embodiment and the foregoing examples, and various modifications may be made. For example, usage applications of the ionic compound of the present application are not limited to the applications herein described, but may include other applications. As other applications, for example, a synthesis catalyst and the like can be cited.

In the foregoing embodiment and the foregoing examples, the description has been given of the case using the electrolytic solution or the using the gel electrolyte in which the electrolytic solution is held by the polymer compound as the electrolyte of the battery of the invention. However, other types of electrolyte may be used. As other electrolyte, for example, a mixture of an ion conductive inorganic compound such as ion conductive ceramics, ion conductive glass, and ionic crystal and an electrolytic solution; a mixture of other inorganic compound and an electrolytic solution; a mixture of the foregoing inorganic compound and a gel electrolyte or the like can be cited.

In the foregoing embodiment and the foregoing examples, the description has been given of the lithium ion secondary battery in which the anode capacity is expressed by the capacity component based on insertion and extraction of lithium, or the lithium metal secondary battery in which the lithium metal is used as an anode active material and the anode capacity is expressed by the capacity component based on precipitation and dissolution of lithium, as the battery of the invention. However, the battery of the invention is not limited thereto. The present application can be similarly applied to a secondary battery in which the anode capacity includes the capacity component based on insertion and extraction of lithium and the capacity component based on precipitation and dissolution of lithium, and the anode capacity is expressed by the sum of these capacity components, by setting the charge capacity of the anode material capable of inserting and extracting lithium to a smaller value than that of the charge capacity of the cathode.

Further, in the foregoing embodiment and the foregoing examples, the description has been given of the case using lithium as an electrode reactant. However, as an electrode reactant, other Group 1A element such as sodium (Na) and potassium (K), a Group 2A element such as magnesium and calcium (Ca), or other light metal such as aluminum may be used. In this case, the anode material described in the foregoing embodiment can be used as an anode active material as well.

Further, in the foregoing embodiment and the foregoing examples, a description has been given with the specific examples of the cylindrical or laminated film type secondary battery as a battery structure of the battery of the invention. However, the battery of the invention can be similarly applied to a secondary battery having other shape such as a coin type battery, a button type battery, and a square battery, or a secondary battery having other structure such as a lamination structure. Further, the battery of the invention can be applied to other batteries such as primary batteries in addition to the secondary batteries.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:
1. An electrolytic solution comprising:
a solvent including 4-fluoro-1,3-dioxolane-2-one (FEC); and
an electrolyte salt,
wherein the electrolyte salt contains an ionic compound selected from the group consisting of [(2,2-bistrifluoromethyl)malonate oxalate]lithium borate, [bis(3,3,3-trifluoromethyl)glycolate oxalate]lithium borate, (2-trifluoromethylpropionate oxalate)lithium borate, (3,3,3-trifluoromethylpropionate oxalate)lithium borate, (difluoroaceto oxalate)lithium borate, (2,3,3,3-tetrafluoropropionate oxalate)lithium borate, (difluoromethanedisulfonate oxalate)lithium borate, and (difluorosulfoaceto oxalate)lithium borate, and wherein the structure of the ionic compound is asymmetric.
2. The electrolytic solution according to claim 1, wherein the solvent also contains a chain ester carbonate having a halogen as an element shown in Chemical formula 3:

Chemical formula 3

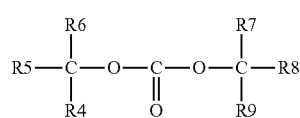

where R4 to R9 represent a hydrogen group, a halogen group, an alkyl group, or an alkyl halide group and are identical or different, but at least one of R4 to R9 is the halogen group or the alkyl halide group.

3. The electrolytic solution according to claim 1, wherein the solvent also contains cyclic ester carbonate having an unsaturated bond.
4. The electrolytic solution according to claim 1, wherein the electrolyte salt further contains at least one selected from the group consisting of lithium hexafluorophospate, lithium tetrafluoroborate, lithium perchlorate, lithium hexafluoroarsenate, and compounds shown in Chemical formulas 5 to 7:

$LiN(C_jF_{2j+1}SO_2)(C_kF_{2k+1}SO_2)$  Chemical formula 5 where j and k represent an integer number of 1 or more, and m and n are identical or different;

Chemical formula 6

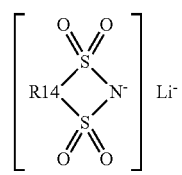

where R14 represents a straight chain or branched perfluoro alkylene group with the carbon number in the range from 2 to 4;

$LiC(C_pF_{2p+1}SO_2)(C_qF_{2q+1}SO_2)(C_rF_{2q+1}SO_2)$  Chemical formula 7 where p, q, and r represent an integer number of 1 or more and are identical or different.

5. An electrochemical device comprising:
an electrolytic solution,
wherein
the electrolytic solution contains a solvent and an electrolyte salt,
the solvent contains 4-fluoro-1,3-dioxolane-2-one (FEC), and
the electrolyte salt contains an ionic compound selected from the group consisting of [(2,2-bistrifluoromethyl)malonate oxalate]lithium borate, [bis(3,3,3-trifluoromethyl)glycolate oxalate]lithium borate, (2-trifluoromethylpropionate oxalate)lithium borate, (3,3,3-trifluoromethylpropionate oxalate)lithium borate, (difluoroaceto oxalate)lithium borate, (2,3,3,3-tetrafluoropropionate oxalate)lithium borate, (difluoromethanedisulfonate oxalate)lithium borate, and (difluorosulfoaceto oxalate)lithium borate, and wherein the structure of the ionic compound is asymmetric.
6. The electrochemical device according to claim 5, wherein the solvent also contains a chain ester carbonate having a halogen as an element shown in Chemical formula 9:

Chemical formula 9

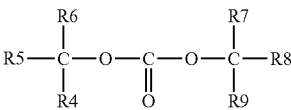

where R4 to R9 represent a hydrogen group, a halogen group, an alkyl group, or an alkyl halide group and are identical or different, but at least one of R4 to R9 is the halogen group or the alkyl halide group.
7. The electrochemical device according to claim 5, wherein the solvent also contains cyclic ester carbonate having an unsaturated bond.
8. The electrochemical device according to claim 5, wherein the electrolyte salt further contains at least one selected from the group consisting of lithium hexafluorophospate, lithium tetrafluoroborate, lithium perchlorate, lithium hexafluoroarsenate, and compounds shown in Chemical formulas 11 to 13:

$$\text{LiN}(C_jF_{2j+1}SO_2)(C_kF_{2k+1}SO_2) \quad \text{Chemical formula 11}$$

where j and k represent an integer number of 1 or more, and m and n are identical or different;

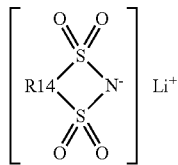

Chemical formula 12 where R14 represents a straight chain or branched perfluoro alkylene group with the carbon number in the range from 2 to 4;

$$\text{LiC}(C_pF_{2p+1}SO_2)(C_qF_{2q+1}SO_2)(C_rF_{2r+1}SO_2) \quad \text{Chemical formula 13}$$

where p, q, and r represent an integer number of 1 or more and are identical or different.

9. A battery comprising:
a cathode;
an anode; and
an electrolytic solution,
wherein the electrolytic solution contains a solvent and an electrolyte salt,
the solvent contains 4-fluoro-1,3-dioxolane-2-one (FEC), and
the electrolyte salt contains an ionic compound selected from the group consisting of [(2,2-bistrifluoromethyl) malonate oxalate]lithium borate, [bis(3,3,3-trifluoromethyl)glycolate oxalate]lithium borate, (2-trifluoromethylpropionate oxalate)lithium borate, (3,3,3-trifluoromethylpropionate oxalate)lithium borate, (difluoroaceto oxalate)lithium borate, (2,3,3,3-tetrafluoropropionate oxalate)lithium borate, (difluoromethanedisulfonate oxalate)lithium borate, and (difluorosulfoaceto oxalate)lithium borate, and wherein the structure of the ionic compound is asymmetric.

10. The battery according to claim 9, wherein the solvent also contains at least one selected from the group consisting of chain ester carbonate having a halogen as an element shown in Chemical formula 15:

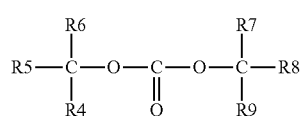

Chemical formula 15 where R4 to R9 represent a hydrogen group, a halogen group, an alkyl group, or an alkyl halide group and are identical or different, but at least one of R4 to R9 is the halogen group or the alkyl halide group.

11. The battery according to claim 10, wherein the chain ester carbonate having a halogen as an element includes at least one of 4-fluoro-1,3-dioxolane-2-one and 4,5-difluoro-1,3-dioxolane-2-one.

12. The battery according to claim 9, wherein the electrolyte salt further contains at least one selected from the group consisting of lithium hexafluorophospate, lithium tetrafluoroborate, lithium perchlorate, lithium hexafluoroarsenate, and compounds shown in Chemical formulas 17 to 19:

$$\text{LiN}(C_jF_{2j+1}SO_2)(C_kF_{2k+1}SO_2) \quad \text{Chemical formula 17}$$

where j and k represent an integer number of 1 or more, and m and n are identical or different;

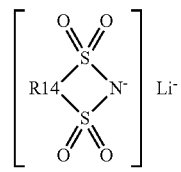

Chemical formula 18 where R14 represents a straight chain or branched perfluoro alkylene group with the carbon number in the range from 2 to 4;

$$\text{LiC}(C_pF_{2p+1}SO_2)(C_qF_{2q+1}SO_2)(C_rF_{2r+1}SO_2) \quad \text{Chemical formula 19}$$

where p, q, and r represent an integer number of 1 or more, and are identical or different.

* * * * *